United States Patent
Rothberg et al.

(10) Patent No.: US 11,494,589 B2
(45) Date of Patent: *Nov. 8, 2022

(54) SYSTEMS AND METHODS FOR UNIFYING STATISTICAL MODELS FOR DIFFERENT DATA MODALITIES

(71) Applicant: Quantum-Si Incorporated, Guilford, CT (US)

(72) Inventors: Jonathan M. Rothberg, Guilford, CT (US); Umut Eser, Lexington, MA (US); Michael Meyer, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/195,311

(22) Filed: Mar. 8, 2021

(65) Prior Publication Data
US 2021/0192290 A1 Jun. 24, 2021

Related U.S. Application Data

(63) Continuation of application No. 16/406,348, filed on May 8, 2019, now Pat. No. 10,956,787.
(Continued)

(51) Int. Cl.
*G06K 9/62* (2022.01)
*G16H 50/70* (2018.01)
(Continued)

(52) U.S. Cl.
CPC ......... *G06K 9/6259* (2013.01); *G06K 9/6269* (2013.01); *G06N 3/08* (2013.01);
(Continued)

(58) Field of Classification Search
CPC ...... G06K 9/6259; G16H 30/40; G16H 50/70; G06N 3/08
See application file for complete search history.

(56) References Cited

U.S. PATENT DOCUMENTS

| 5,961,924 A | 10/1999 | Reichert et al. |
| 6,787,308 B2 | 9/2004 | Balasubramanian et al. |

(Continued)

FOREIGN PATENT DOCUMENTS

| EP | 3 223 183 A1 | 9/2017 |
| WO | WO 2011/153962 A1 | 12/2011 |
| WO | WO 2018/042211 A1 * | 3/2018 |

OTHER PUBLICATIONS

U.S. Appl. No. 16/407,033, filed May 8, 2019, Eser et al..
(Continued)

*Primary Examiner* — Edward Park
(74) *Attorney, Agent, or Firm* — Wolf, Greenfield & Sacks, P.C.

(57) ABSTRACT

Techniques for performing a prediction task using a multi-modal statistical model configured to receive input data from multiple modalities including input data from a first modality and input data from a second modality different from the first modality. The techniques include: obtaining information specifying the multi-modal statistical model including values of parameters of each of multiple components of the multi-modal statistical model, the multiple components including first and second encoders for processing input data for the first and second modalities, respectively, first and second modality embeddings, a joint-modality representation, and a predictor; obtaining first input data for the first data modality; providing the first input data to the first encoder to generate a first feature vector; identifying a second feature vector using the joint-modality representation, the first modality embedding and the first feature vector; and generating a prediction for the prediction task using the predictor and the second feature vector.

20 Claims, 8 Drawing Sheets

Related U.S. Application Data

(60) Provisional application No. 62/678,074, filed on May 30, 2018, provisional application No. 62/671,068, filed on May 14, 2018.

(51) Int. Cl.
*G16H 30/40* (2018.01)
*G06N 3/08* (2006.01)
*G06N 3/04* (2006.01)

(52) U.S. Cl.
CPC .............. *G16H 30/40* (2018.01); *G16H 50/70* (2018.01); *G06N 3/04* (2013.01); *G06N 3/0445* (2013.01)

(56) References Cited

U.S. PATENT DOCUMENTS

| | | | |
|---|---|---|---|
| 6,917,726 | B2 | 7/2005 | Levene et al. |
| 7,175,811 | B2 | 2/2007 | Bach et al. |
| 7,426,322 | B2 | 9/2008 | Hyde |
| 7,738,086 | B2 | 6/2010 | Shepard et al. |
| 7,820,983 | B2 | 10/2010 | Lundquist et al. |
| 7,834,329 | B2 | 11/2010 | Lundquist et al. |
| 7,838,847 | B2 | 11/2010 | Lundquist et al. |
| 8,053,742 | B2 | 11/2011 | Lundquist et al. |
| 8,207,509 | B2 | 6/2012 | Lundquist et al. |
| 8,274,040 | B2 | 9/2012 | Zhong et al. |
| 8,278,728 | B2 | 10/2012 | Murshid |
| 8,465,699 | B2 | 6/2013 | Fehr et al. |
| 8,471,219 | B2 | 6/2013 | Lundquist et al. |
| 8,471,230 | B2 | 6/2013 | Zhong et al. |
| 8,502,169 | B2 | 8/2013 | Rigneault et al. |
| 8,618,507 | B1 | 12/2013 | Lundquist et al. |
| 9,029,802 | B2 | 5/2015 | Lundquist et al. |
| 9,157,864 | B2 | 10/2015 | Fehr et al. |
| 9,222,123 | B2 | 12/2015 | Zhong et al. |
| 9,222,133 | B2 | 12/2015 | Lundquist et al. |
| 9,223,084 | B2 | 12/2015 | Grot et al. |
| 9,372,308 | B1 | 6/2016 | Saxena et al. |
| 9,587,276 | B2 | 3/2017 | Lundquist et al. |
| 9,606,060 | B2 | 3/2017 | Chen et al. |
| 9,658,161 | B2 | 5/2017 | Saxena et al. |
| 9,666,748 | B2 | 5/2017 | Leobandung |
| 9,719,138 | B2 | 8/2017 | Zhong et al. |
| 9,765,395 | B2 | 9/2017 | Goldsmith |
| 9,946,017 | B2 | 4/2018 | Saxena et al. |
| 10,018,764 | B2 | 7/2018 | Grot et al. |
| 10,090,429 | B2 | 10/2018 | Leobandung |
| 10,138,515 | B2 | 11/2018 | Fehr et al. |
| 10,280,457 | B2 | 5/2019 | Zhong et al. |
| 10,310,178 | B2 | 6/2019 | Saxena et al. |
| 10,487,356 | B2 | 11/2019 | Lundquist et al. |
| 10,578,788 | B2 | 3/2020 | Grot et al. |
| 10,655,172 | B2 | 5/2020 | Rank et al. |
| 10,956,787 | B2 | 3/2021 | Rothberg et al. |
| 2002/0182716 | A1 | 12/2002 | Weisbuch et al. |
| 2003/0174992 | A1 | 9/2003 | Levene et al. |
| 2010/0065726 | A1 | 3/2010 | Zhong et al. |
| 2013/0116153 | A1 | 5/2013 | Bowen et al. |
| 2015/0120760 | A1 | 4/2015 | Wang et al. |
| 2016/0170982 | A1 | 6/2016 | Djuric et al. |
| 2016/0253783 | A1* | 9/2016 | Higashi ............... G06T 5/40 382/168 |
| 2017/0146479 | A1 | 5/2017 | Levine et al. |
| 2017/0293736 | A1 | 10/2017 | Kramer et al. |
| 2019/0026655 | A1 | 1/2019 | Xie et al. |
| 2019/0197366 | A1 | 6/2019 | Kecskemethy et al. |
| 2019/0292590 | A1 | 9/2019 | Zhong et al. |
| 2019/0347523 | A1 | 11/2019 | Rothberg et al. |

OTHER PUBLICATIONS

U.S. Appl. No. 16/406,993, filed May 8, 2019, Hernandez et al..
PCT/US2019/031255, dated Jul. 29, 2019, International Search Report and Written Opinion.
PCT/US2019/031260, dated Feb. 18, 2020, International Search Report and Written Opinion.
International Search Report and Written Opinion for International Application No. PCT/US2019/031255 dated Jul. 29, 2019.
International Search Report and Written Opinion for International Application No. PCT/US2019/031260 dated Feb. 18, 2020.
Aliper et al., Deep learning applications for predicting pharmacological properties of drugs and drug repurposing using transcriptomic data. Molecular pharmaceutics. Jul. 5, 2016;13(7):2524-30.
Dudley et al., Computational repositioning of the anticonvulsant topiramate for inflammatory bowel disease. Science translational medicine. Aug. 17, 2011;3(94-98):119-124.
Hale, Fibre Optic Sensors using Adiabatically Tapered Single Mode Fibres. Dissertation submitted to the University of Cambridge. Feb. 1994. 209 pages.
March-Vila et al., On the integration of in silico drug design methods for drug repurposing. Frontiers in pharmacology. May 23, 2017;8:298.
Masood et al., Self-supervised learning model for skin cancer diagnosis. 2015 7th International IEEE/EMBS Conference on Neural Engineering (NER). Apr. 22, 2015:1012-1015.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Napolitano et al., Drug repositioning: a machine-learning approach through data integration. Journal of cheminformatics. Dec. 1, 2013;5(1):30.
Taitt et al., Evanescent wave fluorescence biosensors. Biosens Bioelectron. Jun. 2005;20(12):2470-87. Epub Dec. 8, 2004.
Xu et al., Comparing a knowledge-driven approach to a supervised machine learning approach in large-scale extraction of drug-side effect relationships from free-text biomedical literature. BMC bioinformatics, BioMed Central. Dec. 2015;16(5):S6.
Zhang et al., Towards drug repositioning: a unified computational framework for integrating multiple aspects of drug similarity and disease similarity. American Medical Informatics Association annual symposium proceedings 2014; 1258.

\* cited by examiner

SYSTEMS AND METHODS FOR UNIFYING STATISTICAL MODELS FOR DIFFERENT DATA MODALITIES

CROSS-REFERENCE TO RELATED APPLICATIONS

This application claims priority under 35 U.S.C. § 120 to U.S. application Ser. No. 16/406,348, filed May 8, 2019, and titled "Systems and Methods for Unifying Statistical Models for Different Data Modalities". Application Ser. No. 16/406,348 claims priority under 35 U.S.C. § 119(e) to U.S. Provisional Patent Application No. 62/671,068, filed May 14, 2018, and titled "Systems and Methods for Multi-Modal Prediction", and U.S. Provisional Patent Application No. 62/678,074, filed May 30, 2018, and titled "Systems and Methods for Unifying Statistical Models for Different Data Modalities", each of which is incorporated by reference in its entirety.

BACKGROUND

Machine learning technology is often applied to problems where data from multiple modalities is available. Data may be collected using different acquisition frameworks, each of which may be characterized by respective data sources, data types, data gathering techniques, sensors, and/or environments. Data being associated with one modality may be gathered by using an acquisition framework that is different from the acquisition framework used to gather data associated with a different modality. For example, data gathered by one type of sensor or experimental technique has a different modality from the data gathered by another type of sensor or experimental technique. As another example, data of one type (e.g., image data) is not of the same modality as data of another type (e.g., text data).

There are many conventional statistical models for processing data for a particular modality. For example, convolutional neural networks may be applied to images to solve the problem of identifying objects shown in the images. As another example, recurrent neural networks may be applied to speech data for speech recognition.

It is more challenging, however, to train and use statistical machine learning models that can effectively utilize data from multiple different data modalities. Such multi-modal statistical machine learning models would have wide applicability in a range of fields including medicine and biology, where there is a large number of heterogeneous data sources (e.g., DNA, RNA and protein expression data for a patient, medical images of the patient in one or more modalities, a patient's medical history, information concerning a disease that the patient may have, etc.) that could be brought to bear on a problem of interest (e.g., predicting whether a patient will respond to a particular drug treatment).

SUMMARY

Some embodiments include a method for training a multi-modal statistical model configured to receive input data from multiple modalities including input data from a first modality and input data from a second modality different from the first modality. The method comprises: accessing unlabeled training data including unlabeled training data for the first modality and unlabeled training data for the second modality; accessing labeled training data including labeled training data for the first modality and labeled training data for the second modality; training the multi-modal statistical model in two stages, the multi-modal statistical model comprising multiple components including first and second encoders for processing input data for the first and second modalities, respectively, first and second modality embeddings, a joint-modality representation, and a predictor, the training comprising: performing a first training stage at least in part by estimating values for parameters of the first and second modality embeddings, and the joint-modality representation using a self-supervised learning technique and the unlabeled training data; performing a second training stage at least in part by estimating values for parameters of the predictor using a supervised learning technique and the labeled training data; and storing information specifying the multi-modal statistical model at least in part by storing the estimated values for parameters of the multiple components of the multi-modal statistical model.

Some embodiments include a system comprising: at least one computer hardware processor; and at least one non-transitory computer-readable storage medium storing processor-executable instructions that, when executed by the at least one computer hardware processor, cause the at least one computer hardware processor to perform a method for training a multi-modal statistical model configured to receive input data from multiple modalities including input data from a first modality and input data from a second modality different from the first modality. The method comprises: accessing unlabeled training data including unlabeled training data for the first modality and unlabeled training data for the second modality; accessing labeled training data including labeled training data for the first modality and labeled training data for the second modality; training the multi-modal statistical model in two stages, the multi-modal statistical model comprising multiple components including first and second encoders for processing input data for the first and second modalities, respectively, first and second modality embeddings, a joint-modality representation, and a predictor, the training comprising: performing a first training stage at least in part by estimating values for parameters of the first and second modality embeddings, and the joint-modality representation using a self-supervised learning technique and the unlabeled training data; performing a second training stage at least in part by estimating values for parameters of the predictor using a supervised learning technique and the labeled training data; and storing information specifying the multi-modal statistical model at least in part by storing the estimated values for parameters of the multiple components of the multi-modal statistical model.

Some embodiments include at least one non-transitory computer-readable storage medium storing processor-executable instructions that, when executed by at least one computer hardware processor, cause the at least one computer hardware processor to perform a method for training a multi-modal statistical model configured to receive input data from multiple modalities including input data from a first modality and input data from a second modality different from the first modality. The method comprises: accessing unlabeled training data including unlabeled training data for the first modality and unlabeled training data for the second modality; accessing labeled training data including labeled training data for the first modality and labeled training data for the second modality; training the multi-modal statistical model in two stages, the multi-modal statistical model comprising multiple components including first and second encoders for processing input data for the first and second modalities, respectively, first and second modality embeddings, a joint-modality representation, and a predictor, the training comprising: performing a first training stage at least in part by estimating values for parameters of the first and second modality embeddings, and the joint-modality representation using a self-supervised learning technique and the unlabeled training data; performing a second training stage at least in part by estimating values for parameters of the predictor using a supervised learning technique and the labeled training data; and storing information specifying the multi-modal statistical model at least in part by storing the estimated values for parameters of the multiple components of the multi-modal statistical model.

In some embodiments, training the multi-modal statistical model further comprises estimating values for parameters of the first and second encoders prior to the first training stage.

In some embodiments, training the multi-modal statistical model further comprises estimating values for parameters of first and second decoders for the first and second modalities, respectively, prior to the first training stage.

In some embodiments, training the multi-modal statistical model further comprises estimating, during the first training stage, values for parameters of the first and second encoders jointly with estimating values of parameters of the joint modality representation.

In some embodiments, training the multi-modal statistical model further comprises estimating, during the first training stage, values for parameters of a first decoder for the first modality and a second decoder for the second modality.

In some embodiments, performing the first training stage comprises: accessing a first data input in the unlabeled training data for the first modality; providing the first data input to the first encoder to generate a first feature vector; identifying a second feature vector using the joint-modality representation, the first modality embedding and the first feature vector; and providing the second feature vector as input to a first decoder to generate a first data output.

In some embodiments, the method further comprises: comparing the first data output with the first data input; and updating at least one value of at least one parameter of the joint-modality representation based on results of the comparison.

In some embodiments, performing the first training stage comprises: accessing a first input in the unlabeled training data for the first modality; providing the first input data to the first encoder to generate a first feature vector; identifying a second feature vector using the joint-modality representation, the second modality embedding and the first feature vector; and providing the second feature vector as input to a second decoder for the second modality to generate a second output data.

In some embodiments, the first encoder is configured to output a d-dimensional vector, and wherein the joint-modality representation comprises N m-dimensional vectors, and wherein the first modality embedding comprises m*d weights.

In some embodiments, identifying the second feature vector using the joint-modality representation, the first feature vector, and the first modality embedding comprises: projecting the joint modality representation to a space of the first modality by using the first modality embedding to obtain N d-dimensional vectors; and identifying, from among the N d-dimensional vectors in the joint-modality representation, a third feature vector most similar to the first feature vector according to a similarity metric; and generating the second feature vector by aggregating the first feature vector with the third feature vector.

In some embodiments, identifying the second feature vector using the joint-modality representation, the first feature vector, and the first modality embedding comprises: projecting the joint modality representation to a space of the first modality by using the first modality embedding to obtain N d-dimensional vectors; calculating weights for at least some of the N d-dimensional vectors in the joint modality representation according to a similarity between the at least some of the N d-dimensional vectors and the first feature vector; and generating the second feature vector by aggregating the first feature vector with the weighted sum of the at least some of the N d-dimensional vectors weighted by the calculated weights.

In some embodiments, the multi-modal statistical model further comprises first and second task embeddings, wherein training the multi-modal statistical model further comprises estimating, during the second training stage, values for parameters of the first and second task embeddings jointly with estimating values of parameters of the predictor.

In some embodiments, the first encoder comprises a neural network. In some embodiments, the neural network is a convolutional neural network. In some embodiments, the neural network is a recurrent neural network.

In some embodiments, the first training stage comprises estimating the values for the parameters of the joint-modality representation using a stochastic gradient descent technique. In some embodiments, the first training stage further comprises estimating the values for the parameters of the first and second modality embeddings using the stochastic gradient descent technique.

In some embodiments, unlabeled training data for the first modality comprises images. In some embodiments, unlabeled training data for the second modality comprises text. In some embodiments, unlabeled training data for the first modality comprises protein sequence data. In some embodiments, unlabeled training data for the second modality comprises protein family data, biological process ontology data, molecular function ontology data, cellular component ontology data, or taxonomic species family data.

In some embodiments, the method further comprises: accessing unlabeled training data for a third modality; accessing labeled training data for the third modality; augmenting the multi-modal statistical model to include a third encoder for the third modality and a third modality embedding; updating the multi-modal statistical model by: updating values for parameters of the third modality embedding, and the joint-modality representation using a self-supervised learning technique and the unlabeled training data for the third modality; and updating values for parameters of the predictor using a supervised learning technique and the labeled training data for the third modality.

In some embodiments, the multi-modal statistical model is configured to receive input data from a third modality different from the first and second modalities and further comprises a third modality embedding, wherein: accessing the unlabeled training data comprises accessing unlabeled training data for the third modality; accessing the labeled training data comprises accessing labeled training data for the third modality; performing the first training stage further comprises estimating values for parameters of the third modality embedding further based on the unlabeled training data for the third modality; performing the second training stage comprises estimating values for parameters of the predictor further based on the labeled training data for the third modality.

Some embodiments include a method for performing a prediction task using a multi-modal statistical model configured to receive input data from multiple modalities including input data from a first modality and input data from a second modality different from the first modality. The method comprises obtaining information specifying the multi-modal statistical model including values of parameters of each of multiple components of the multi-modal statistical model, the multiple components including first and second encoders for processing input data for the first and second modalities, respectively, first and second modality embeddings, a joint-modality representation, and a predictor; obtaining first input data for the first data modality; providing the first input data to the first encoder to generate a first feature vector; identifying a second feature vector using the joint-modality representation, the first modality embedding and the first feature vector; and generating a prediction for the prediction task using the predictor and the second feature vector.

Some embodiments include a system for performing a prediction task using a multi-modal statistical model configured to receive input data from multiple modalities including input data from a first modality and input data from a second modality different from the first modality. The system comprises: at least one computer hardware processor; and at least one non-transitory computer-readable storage medium storing processor executable instructions that, when executed by the at least one computer hardware processor, causes the at least one computer hardware processor to perform: obtaining information specifying the multi-modal statistical model including values of parameters of each of multiple components of the multi-modal statistical model, the multiple components including first and second encoders for processing input data for the first and second modalities, respectively, first and second modality embeddings, a joint-modality representation, and a predictor; obtaining first input data for the first data modality; providing the first input data to the first encoder to generate a first feature vector; identifying a second feature vector using the joint-modality representation, the first modality embedding and the first feature vector; and generating a prediction for the prediction task using the predictor and the second feature vector.

Some embodiments include at least one non-transitory computer-readable storage medium storing processor executable instructions that, when executed by the at least one computer hardware processor, causes the at least one computer hardware processor to perform: obtaining information specifying the multi-modal statistical model including values of parameters of each of multiple components of the multi-modal statistical model, the multiple components including first and second encoders for processing input data for the first and second modalities, respectively, first and second modality embeddings, a joint-modality representation, and a predictor; obtaining first input data for the first data modality; providing the first input data to the first encoder to generate a first feature vector; identifying a second feature vector using the joint-modality representation, the first modality embedding and the first feature vector; and generating a prediction for the prediction task using the predictor and the second feature vector.

In some embodiments, the method further comprises: obtaining second input data for the second data modality; providing the second input data to the second encoder to generate a third feature vector; identifying a fourth feature vector using the joint-modality representation, the second modality embedding and the third feature vector, wherein generating the prediction for the prediction task is performed using the fourth feature vector.

In some embodiments, the multi-modal statistical model comprises first and second task embeddings for the first and second modalities, and wherein generating the prediction for the prediction task further comprises: weighting the second feature vector using the first task embedding; weighting the fourth feature vector using the second task embedding; and generating the prediction for the prediction task using the weighted second and fourth feature vectors and the predictor.

In some embodiments, the method further comprises: providing the weighted second and fourth feature vectors to the predictor.

In some embodiments, the first encoder is configured to output a d-dimensional vector, and wherein the joint-modality representation comprises N of m-dimensional vectors, and wherein the first modality embedding comprises m×d weights.

In some embodiments, identifying the second feature vector using the joint-modality representation, the first feature vector, and the first modality embedding comprises: projecting the joint modality representation to a space of the first modality by using the first modality embedding to obtain N d-dimensional vectors; identifying, from among the N d-dimensional vectors in the joint-modality representation, a third feature vector most similar to the first feature vector according to a similarity metric; and generating the second feature vector by weighting dimensions of the third feature vector using weights in the first modality embedding.

In some embodiments, identifying the second feature vector using the joint-modality representation, the first feature vector, and the first modality embedding comprises: projecting the joint modality representation to a space of the first modality by using the first modality embedding to obtain N d-dimensional vectors; identifying, from among the N d-dimensional vectors in the joint-modality representation, a third feature vector most similar to the first feature vector according to a similarity metric; and generating the second feature vector by aggregating the first feature vector and the third feature vector.

In some embodiments, identifying the second feature vector using the joint-modality representation, the first feature vector, and the first modality embedding comprises: projecting the joint modality representation to a space of the first modality by using the first modality embedding to obtain N d-dimensional vectors; calculating weights for at least some of the N d-dimensional vectors in the joint modality representation according to a similarity between the at least some of the N d-dimensional vectors and the first feature vector; and generating the second feature vector as a weighted sum of the at least some of the N d-dimensional vectors weighted by the calculated weights.

In some embodiments, the first encoder comprises a neural network. In some embodiments, the neural network is a convolutional neural network. In some embodiments, the neural network is a recurrent neural network.

In some embodiments, input data for the first modality comprises at least one image. In some embodiments, input data for the second modality comprises text. In some embodiments, input data for the first modality comprises protein sequence data. In some embodiments, input data for the second modality comprises protein family data, biological process ontology data, molecular function ontology data, cellular component ontology data, or taxonomic species family data.

It should be appreciated that all combinations of the foregoing concepts and additional concepts discussed in greater detail below (provided such concepts are not mutually inconsistent) are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

DETAILED DESCRIPTION

Figure 1:
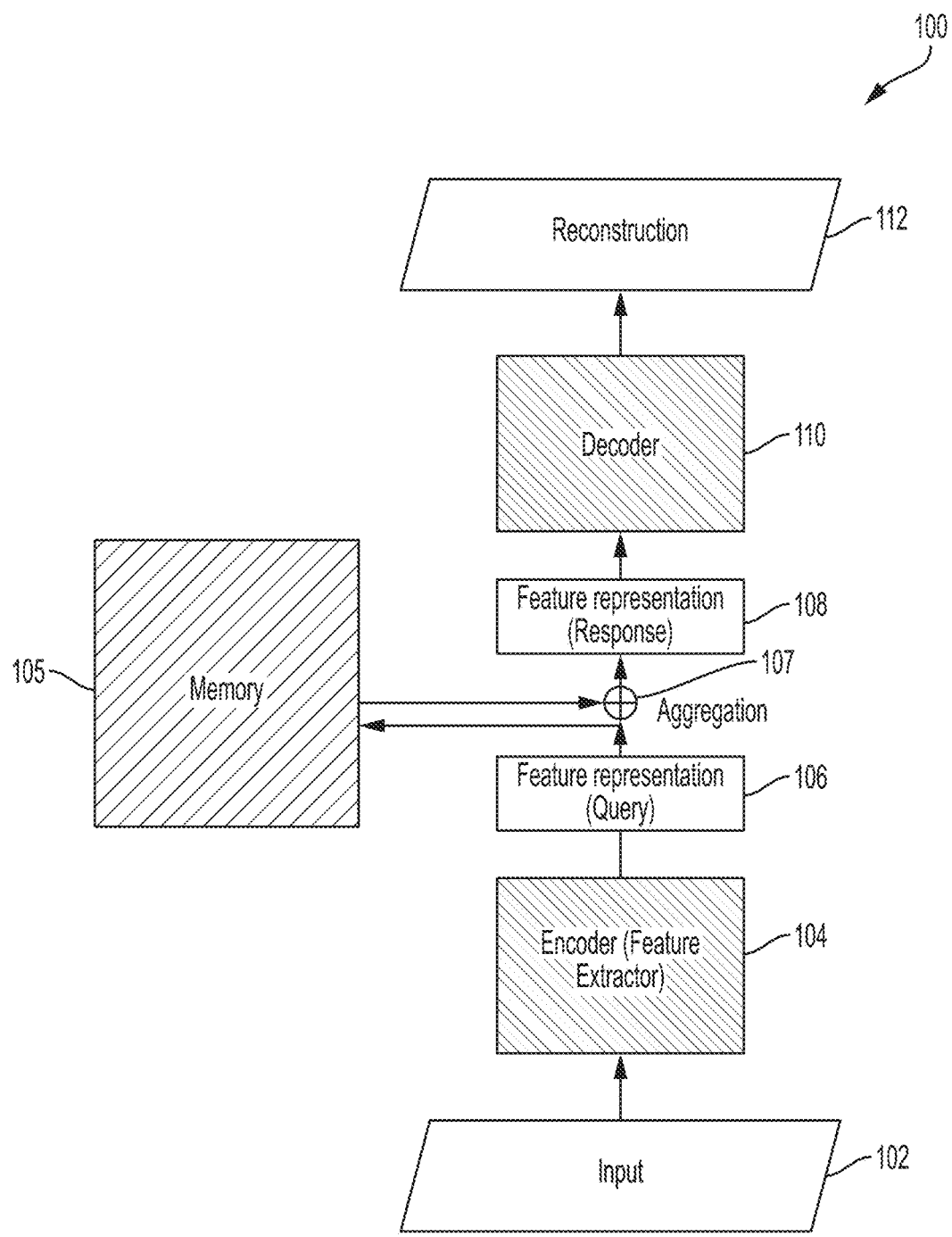
FIG. 1 is a diagram illustrating training of a knowledge base for a statistical model for a single modality using a self-supervised learning technique, in accordance with some embodiments of the technology described herein.

A statistical model configured receive, as input, and process, data from multiple modalities may be referred to as a multi-modal statistical model. The inventors have developed a new class of multi-modal statistical models by developing novel techniques for integrating multiple individual statistical models, each designed to process data in a different respective modality, to generate multi-modal statistical models. The techniques described herein may be used to integrate multiple deep learning models trained for different modalities and/or any other suitable types of statistical models. The techniques developed by the inventors address drawbacks of conventional techniques for building multi-modal statistical models. By addressing these drawbacks, the inventors have developed technology that improves upon conventional machine learning systems and the computer technology used to implement them.

Conventional machine learning techniques for training a multi-modal statistical model require that the multi-modal statistical model be trained "synchronously" using linked data from each of the multiple modalities, whereby each piece of training data includes data from each of the modalities the statistical model is being trained to process. The requirement for such concurrent training is a severe limitation and prevents the design of multi-modal statistical models that can receive and process data from more than a handful of (e.g., 2 or 3) modalities, whereas multi-modal statistical models that can input process a much greater number of data modalities are needed, especially in fields such as medicine and biology.

Synchronous training is a severe limitation because it requires collecting linked data—each piece of training data for one modality must have a corresponding piece of training data in every other modality that the multi-modal statistical model is being trained to process. Collecting such training data is prohibitively expensive and extremely time-consuming, requiring hundreds or thousands of man hours to collect and label the data. Even if concurrent training were possible and linked data were available for two data modalities, if at a later time new data for another data modality were obtained, the new data would have to be linked (again time consuming and expensive) to the existing data, and the entire statistical model would have to be re-trained. In sum, synchronous training makes it impractical, and near-impossible in practice, to generate and update multi-modal statistical models for more than a small number (i.e., 2 or 3) modalities.

The techniques developed by the inventors and described herein allow for efficiently creating and updating of multi-modal statistical models without requiring that training be performed synchronously using linked data from each of the multiple modalities that the statistical model is being trained to process. In contrast to conventional techniques, the inventors have developed an approach that allows for asynchronous training and updating of multi-modal statistical models. The asynchronous training is enabled by the innovative shared code-book architecture described herein. In this architecture, individual statistical models, previously trained for processing data in respective modalities, are integrated by coupling their respective latent representations to a joint modality representation, which allows information among the individual models to be shared.

The inventors have not only developed an innovative architecture for integrating individual statistical models, but have also specified novel algorithms for asynchronously training components of this architecture using training data from each of multiple modalities, and updating the parameters of the trained components as additional data becomes available. The techniques described herein can be applied to training a multi-modal statistical model to receive and process data for any suitable number of data modalities (e.g., two, three, four, five, six, seven, eight, nine, ten, eleven, twelve, thirteen, fourteen, fifteen, sixteen, etc.). As described below with reference to FIG. 5, the inventors have used the new techniques to generate a multi-modal statistical model for processing data arising in six different modalities (for the problem of protein structure prediction), which would not be possible with conventional techniques.

Utilizing asynchronous training not only provides an improvement over conventional techniques in that it, for the first time, enables generating multi-modal statistical models for any suitable number of data modalities, but also improves the computer technology used to train and deploy such machine learning systems. In particular, the multi-modal statistical models described herein may be trained with less training data (because linked training data instances across all modalities are not required), which in turn means that fewer computing resources need to be used to train and deploy such models. Specifically, less processor power and time is needed, less memory is needed, and less networking resources (e.g., network bandwidth) is needed for the transmission of such data, all of which directly improves computer functionality.

The techniques developed by the inventors may be referred to, at times, as the "UNITY" framework, as they allow for the efficient unification of statistical models built for different data modalities through the techniques of training and using multi-modal statistical models developed by the inventors and described herein.

Accordingly, some embodiments, provide for techniques for training a multi-modal statistical model configured to receive input data from multiple modalities including input data from a first modality and input data from a second modality different from the first modality. The techniques include: (1) accessing unlabeled training data including unlabeled training data for the first modality and unlabeled training data for the second modality; (2) accessing labeled training data including labeled training data for the first modality and labeled training data for the second modality; (3) training the multi-modal statistical model in two stages, the multi-modal statistical model comprising multiple components including first and second encoders for processing input data for the first and second modalities, respectively, first and second modality embeddings, a joint-modality representation, and a predictor, the training comprising: (A) performing a first training stage at least in part by estimating values for parameters of the first and second modality embeddings, and the joint-modality representation using a self-supervised learning technique and the unlabeled training data; (B) performing a second training stage at least in part by estimating values for parameters of the predictor using a supervised learning technique and the labeled training data; and (4) storing information specifying the multi-modal statistical model at least in part by storing the estimated values for parameters of the multiple components of the multi-modal statistical model.

In some embodiments, the parameters of the first and second encoders may be estimated prior to the first training stage of the multi-modal statistical model. This may the case when individual statistical models being integrated have been previously trained and the parameters of their respective encoders have been estimated. In other embodiments, the parameters of the encoders may be estimated for the first time and/or updated during the training of the multi-modal statistical model. Similarly, the first and second decoders may be trained prior to or during the training of the multi-modal statistical modal.

In some embodiments, the joint modality representation may be a code-book including N m-dimensional vectors. Each individual statistical model being integrated may be configured to: generate a latent representation of its input and use this latent representation to identify a similar vector or vectors in the joint modality representation. In turn, the identified vector(s) may be used to generate a new set of features that can be used for a prediction task. In this way, features generated for one modality may be updated to reflect, through the use of a common code-book, information gathered in a different modality.

In some embodiments, performing the first training stage comprises: (A) accessing a first data input in the unlabeled training data for the first modality; (B) providing the first data input to the first encoder to generate a first feature vector; (C) identifying a second feature vector using the joint-modality representation, the first modality embedding and the first feature vector; (D) providing the second feature vector as input to a first decoder to generate a first data output. The first data output may then be compared with the first data input, and one or more parameter values of the joint-modality representation may be updated based on results of the comparison (e.g., using stochastic gradient descent).

In some embodiments, identifying the second feature vector using the joint-modality representation, the first feature vector, and the first modality embedding comprises: (A) projecting the joint modality representation to a space of the first modality by using the first modality embedding to obtain N d-dimensional vectors; (B) calculating weights for at least some of the N d-dimensional vectors in the joint modality representation according to a similarity between the at least some of the N d-dimensional vectors and the first feature vector; and (C) generating the second feature vector by aggregating the first feature vector with the weighted sum of the at least some of the N d-dimensional vectors weighted by the calculated weights.

In some embodiments, the multi-modal statistical model being trained further comprises first and second task embeddings, wherein training the multi-modal statistical model further comprises estimating, during the second training stage, values for parameters of the first and second task embeddings jointly with estimating values of parameters of the predictor.

In some embodiments, the first encoder may be a neural network such as a convolutional neural network, a recurrent neural network, or any other suitable type of statistical model.

In some embodiments, the unlabeled training data for the first modality comprises images and the unlabeled training data for the second modality comprises text. In some embodiments, the unlabeled training data for the first modality comprises protein sequence data and the unlabeled training data for the second modality comprises protein family data, biological process ontology data, molecular function ontology data, cellular component ontology data, or taxonomic species family data.

Some embodiments include techniques for performing a prediction task using a multi-modal statistical model configured to receive input data from multiple modalities including input data from a first modality and input data from a second modality different from the first modality. The techniques include: (A) obtaining information specifying the multi-modal statistical model including values of parameters of each of multiple components of the multi-modal statistical model, the multiple components including first and second encoders for processing input data for the first and second modalities, respectively, first and second modality embeddings, a joint-modality representation, and a predictor; (B) obtaining first input data for the first data modality; (C) providing the first input data to the first encoder to generate a first feature vector; (D) identifying a second feature vector using the joint-modality representation, the first modality embedding and the first feature vector; and (E) generating a prediction for the prediction task using the predictor and the second feature vector.

In some embodiments, the techniques may further include: (A) obtaining second input data for the second data modality; (B) providing the second input data to the second encoder to generate a third feature vector; (C) identifying a fourth feature vector using the joint-modality representation, the second modality embedding and the third feature vector. Generating the prediction for the prediction task may be performed using the second feature vector and the fourth feature vector.

In some embodiments, the multi-modal statistical model may comprises first and second task embeddings for the first and second modalities, and generating the prediction for the predict task may include: weighting the second feature vector using the first task embedding; weighting the fourth feature vector using the second task embedding; and generating the prediction for the prediction task using the weighted second and fourth feature vectors and the predictor.

It should be appreciated that the techniques introduced above and discussed in greater detail below may be implemented in any of numerous ways, as the techniques are not limited to any particular manner of implementation. Examples of details of implementation are provided herein solely for illustrative purposes. Furthermore, the techniques disclosed herein may be used individually or in any suitable combination, as aspects of the technology described herein are not limited to the use of any particular technique or combination of techniques.

FIG. 1 is a diagram illustrating training of a knowledge base for a statistical model 100 for a single modality using a self-supervised learning technique, in accordance with some embodiments of the technology described herein. The statistical model 100 includes a number of components having respective parameters including encoder 104, decoder 110, and memory 105 representing a knowledge base.

In this example, it is assumed that the encoder 104 and decoder 110 have been previously trained as shown by the fill pattern having diagonal lines extending downward from left to right and that the memory 105 is not yet trained, as shown by the fill pattern having diagonal lines extending upward from left to right. However, as described in more detail below, in some embodiments, the individual statistical models may be trained for the first time or at least updated during training of the multi-modal statistical model.

In some embodiments, encoder 104 may be configured to receive input and output a latent representation (which may have a lower dimensionality than the dimensionality of the input data) and the first decoder may be configured to reconstruct the input data from the latent representation. In some embodiments, the encoder and decoder may be part of an auto-encoder. In some embodiments, the statistical model 100 may be neural network model and the encoder 104 and the decoder 110 may include one or more neural network layers such that the parameters of the encoder 104 and decoder 110 include weights for each of the neural network layers. Though it should be appreciated that the encoder 104 and decoder 110 are not limited to being neural networks and may be any other suitable type of statistical model.

In some embodiments, parameters values for the memory 105 may be estimated using self-supervised learning, so that the output of statistical model 100 reproduces the inputs to the statistical model 100 as closely as possible. Accordingly, in some embodiments, during training, output of the statistical model 100 is compared to the input and the parameter values of the memory 105 are updated iteratively, based on a measure of distance between the input and the output, using stochastic gradient descent (with gradients calculated using backpropagation when the encoder and decoder are neural networks) or any other suitable training algorithm.

For example, in some embodiments, training data may be provided as input 102 to the first encoder 104. Encoder 104 generates, based on the input 102, the first feature representation 106. The feature representation 106 is used to obtain, using the memory 105, a second feature representation 108. In some embodiments, the memory 105 may store a plurality of vectors having the same dimensionality as that of feature representation 106. For example, the feature representation 108 may be a d-dimensional vector and the memory 105 may store N d-dimensional vectors. In some embodiments, the second feature representation 108 may be obtained by selecting, from among the vectors in memory 105, the vector most similar (according to a suitable measure of similarity such as cosine similarity, Euclidean distance, etc.) to the first feature representation 106 and adding the selected vector to the feature representation 106 via aggregation operation 107 (which may be summation, multiplication, arithmetic averaging, geometric averaging, or any other suitable operation). In some embodiments, the second feature representation 108 may be generated by aggregating with feature representation 106 a weighted linear combination of the vectors in memory 105, with the weight for each vector being proportional to the distance between the vector and the feature representation 106. The second feature representation is provided as input to decoder 110. In turn, the output of decoder 110 may be compared with the input provided to the encoder 104, and at least some of the parameter values of the memory 105 may be updated based on the difference between the input to encoder 104 and the output of decoder 110.

Although in the embodiment explained with reference to FIG. 1, it was assumed that encoder 104 and decoder 110 have been trained, in other embodiments, the parameter values of encoder 104 and decoder 110 may be estimated for the first time and/or updated at the same time as the parameter values of memory 105 are being estimated.

The illustrative example of FIG. 1 is helpful for understanding the techniques developed by the inventors for integrating multiple previously-trained statistical models into a single multi-modal statistical model. In particular, as described herein, the multi-modal statistical model allows for sharing of information among different modalities through a joint modality representation. Like the memory 105, which is accessed during training and use of statistical model 100 for a single modality, the joint modality representation (e.g., knowledge base 230 shown in FIGS. 2A and 2B), is accessed during training and use of multi-modal statistical models (e.g., model 250) described herein.

As described herein, when the joint modality representation is accessed to perform calculations for one modality, its contents may be first projected to that modality using a modality embedding. Such modality projections forms part of the multi-modal statistical models described herein.

As described in connection with FIG. 1, the single-modality statistical model 100 includes memory 105, which may be trained using self-supervised learning using previously-trained encoder 104, decoder 110, and training data (which need not be labeled with respect to any classification task). The multi-modal statistical model developed by the inventors (e.g., multi-modal statistical model 250) includes a joint modality representation (e.g., knowledge base 230) and multiple modality embeddings (e.g., modality embeddings 232), which may be trained using self-supervised learning, as described herein including with reference FIGS. 2A, 2B, and 3, and used for prediction, as described herein including with reference to FIGS. 2B and 4.

Figure 2A:
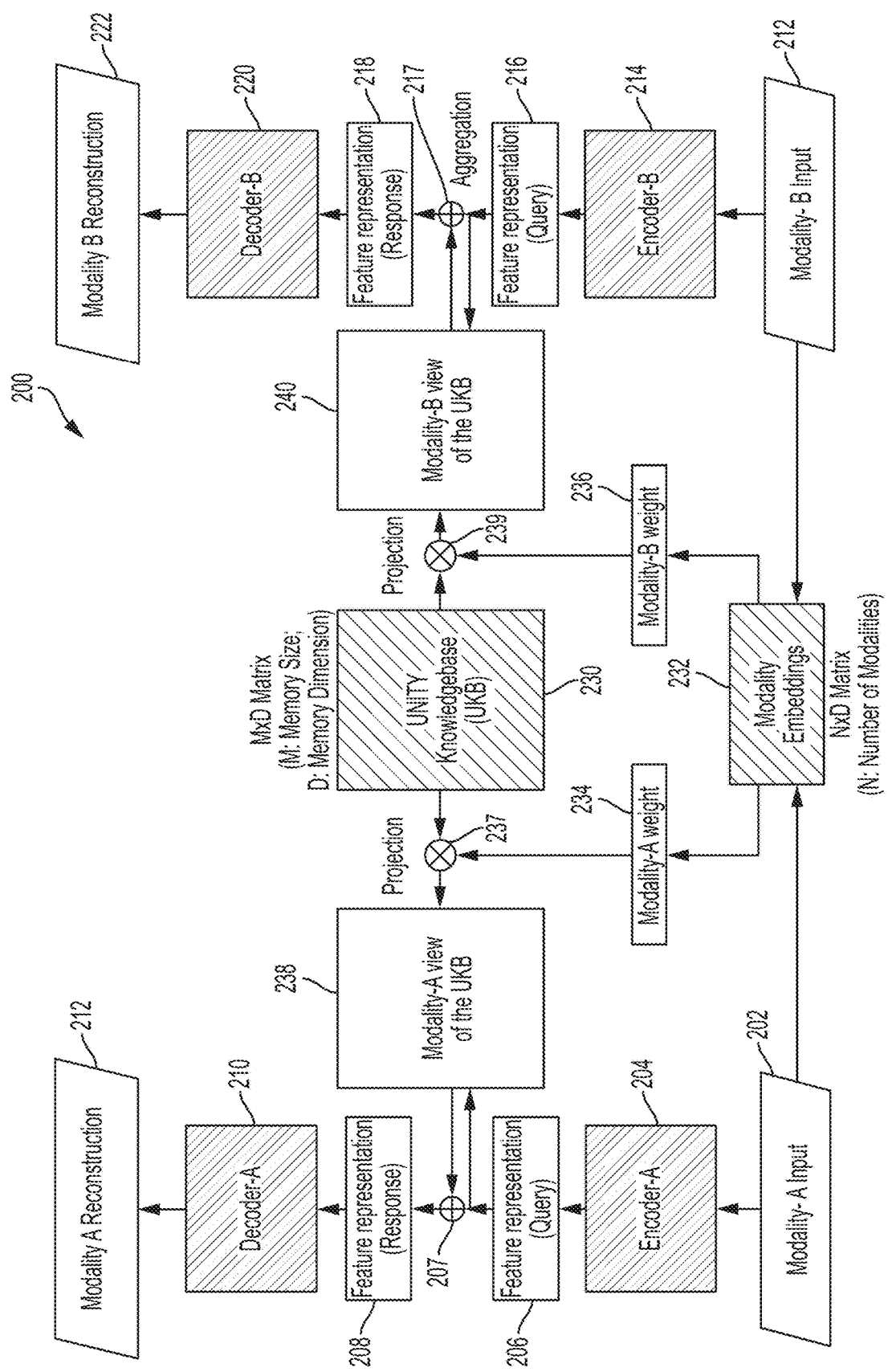
FIG. 2A is a diagram illustrating a first training stage of a multi-modal statistical model using a self-supervised learning technique, in accordance with some embodiments of the technology described herein.
Figure 2B:
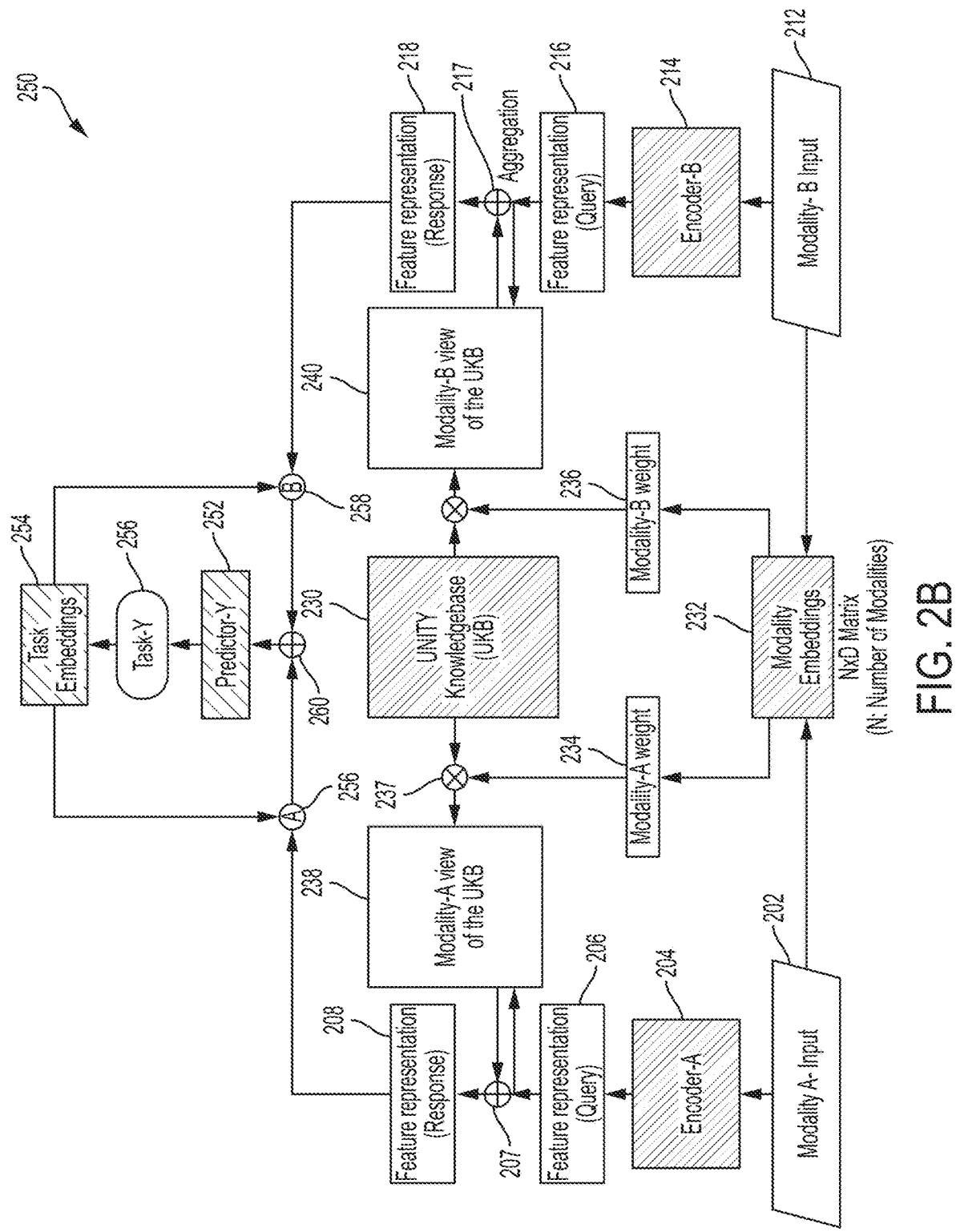
FIG. 2B is a diagram illustrating a second training stage of the multi-modal statistical model using a supervised learning technique, in accordance with some embodiments of the technology described herein.

In some embodiments, the multi-modal statistical model developed by the inventors may be trained using a two-stage training procedure. The first training stage is performed using a self-supervised training technique and involves learning parameters of the joint modality representation and modality embeddings. The second stage is performed using a supervised training technique and involves learning parameters of a predictor (for an appropriate prediction task) and task embeddings. FIGS. 2A and 2B illustrate which components of the multi-modal statistical model are learned in each of these two stages, in some embodiments.

FIG. 2A is a diagram illustrating a first training stage of a multi-modal statistical model using a self-supervised learning technique, in accordance with some embodiments of the technology described herein. As shown in FIG. 2A, the statistical model includes a number of components having respective parameters including an encoder 204 for the first modality, an encoder 214 for the second modality, a knowledge base 230, and modality embeddings 232, which includes a modality embedding for each of the first and second modalities. Additionally, as shown in FIG. 2A, the training environment 200 includes decoder 210 for the first modality and the decoder 220 for the second modality. These decoders are not part of the multi-modal statistical model, rather the decoders are used for training the multi-modal statistical model in the self-supervised training stage; they are not used for prediction as may be seen from FIG. 2B.

In the embodiment illustrated in FIG. 2A, it is assumed that the encoders 204 and 214, and the decoders 210 and 220, have been previously trained as shown by the fill pattern having diagonal lines extending downward from left to right, and that the knowledge base 230 and the modality embeddings 232 are not yet trained, as shown by the fill pattern having diagonal lines extending upward from left to right. However, as described herein in some embodiments, one or more of the encoders and decoders may be trained for the first time or at least updated during training of the multi-modal statistical model.

In some embodiments, each of encoder 204, encoder 214, decoder 210 and decoder 220 may be a respective neural network comprising one or more neural network layers. The layers may include one or more convolutional layers, one or more pooling layers, one or subsampling layers, one or more fully connected layers, and/or any other suitable layer(s). However, none of encoders 204 and 214, and decoders 210 and 220 are limited to be a neural network model and may be any other suitable type of statistical model(s), as aspects of the technology described herein are not limited in this respect.

In some embodiments, the knowledge base 230 (which is an example of a joint modality representation) may include N m-dimensional vectors. These vectors may be stored and/or represented using a matrix (e.g., an N×m matrix) or any other suitable data structure(s), as aspects of the technology described herein are not limited in this respect.

In some embodiments, each modality embedding may be configured to project the knowledge base 230 into the respective modality space. For example, in some embodiments, the modality embedding (of modality embeddings 232) for the first modality may be used to project, using projection operation 237, the knowledge base 230 to the first modality in order to obtain a first modality view 238 of the knowledge base 230. The projection operation may make use of weights 234 part of the modality embedding for the first modality. As another example, in some embodiments, the modality embedding (of modality embeddings 232) for the second modality may be used to project, using projection operation 239, the knowledge base 230 to the second modality in order to obtain a second modality view 240 of the knowledge base 230. The projection operation may make use of weights 236 part of the modality embedding for the second modality.

In some embodiments, each modality embedding may be configured to project the knowledge base 230 into the respective modality space such that the dimensionality of the vectors in the projected knowledge base match the dimensionality of the latent representation in that modality space. For example, suppose the knowledge base 230 includes N m-dimensional vectors, with N=512 and m=64, and that the latent representation generated by the encoder for the first modality is a d-dimensional vector with d=10. In this example, the modality embedding for the first modality may be an m×d (a 64×10) matrix, which when applied to the 512×64 knowledge base 230 generates a 512×10 view of the knowledge base 230 for the first modality. Suppose further that the latent representation generated by the encoder for the second modality is a p-dimensional vector with p=12. Then, the modality embedding for the first modality may be an m×p (a 64×12) matrix, which when applied to the 512×64 knowledge base 230 generates a 512×12 view of the knowledge base 230 for the second modality. As may be appreciated from the foregoing example, the modality embeddings, among other things, allow for the integration of statistical models for different modalities in a situation where the dimensionality of the latent representations in not the same (e.g., 10-dimensional in one modality and 12-dimensional in another modality).

Aspects of the first (self-supervised) training stage of the multi-modal statistical model are described in more detail below with reference to FIG. 3.

FIG. 2B is a diagram illustrating a second training stage of the multi-modal statistical model 250 using a supervised learning technique, in accordance with some embodiments of the technology described herein. As shown in FIG. 2B, the multi-modal statistical model 250 includes predictor 252 for prediction task 256 and task embeddings 254.

In the embodiment illustrated in FIG. 2B, it is assumed that the encoders 204 and 214, the decoders 210 and 220, the knowledge base 230, and the modality embeddings 232 have been previously trained as shown by the fill pattern having diagonal lines extending downward from left to right, and that the predictor 252 and task embeddings 254, as shown by the fill pattern having diagonal lines extending upward from left to right. However, as described herein, in some embodiments, one or more of the encoders, decoders, modality embeddings, and joint modality representation may be trained for the first time or at least updated during the second stage of training of the multi-modal statistical model.

In some embodiments, the predictor 252 may be of any suitable type statistical model mapping input features to an output (e.g., a discrete label in the case of a classifier or continuous variable in the case of a regressor). For example, the predictor 252 may comprise a linear model (e.g., a linear regression model), a generalized linear model (e.g., logistic regression, probit regression), a neural network or other non-linear regression model, a Gaussian mixture model, a support vector machine, a decision tree model, a random forest model, a Bayesian hierarchical model, a Markov random field, and/or any other suitable type of statistical model, as aspects of the technology described herein are not limited in this respect.

In some embodiments, the task embeddings 254 may be used to weight, via operations 256 and 258, the contribution of features from the first and second modalities. For example, as shown in FIG. 2B, the feature representation 208 may be weighted, via operation 256, using the task embedding for the first modality and the feature representation 218 may be weighted, via operation 258, using the task embedding for the second modality. These weighted feature representations may then be aggregated (e.g., as a weighted sum or product) via operation 260 to generate input for the predictor 252. The weighting induced by a task embedding to a feature representation may be a point-wise multiplicative weighting (e.g., a Hadamard product).

Aspects of the second (supervised) training stage of the multi-modal statistical model are described in more detail below with reference to FIG. 3.

Training Multi-Modal Statistical Models

Figure 3:
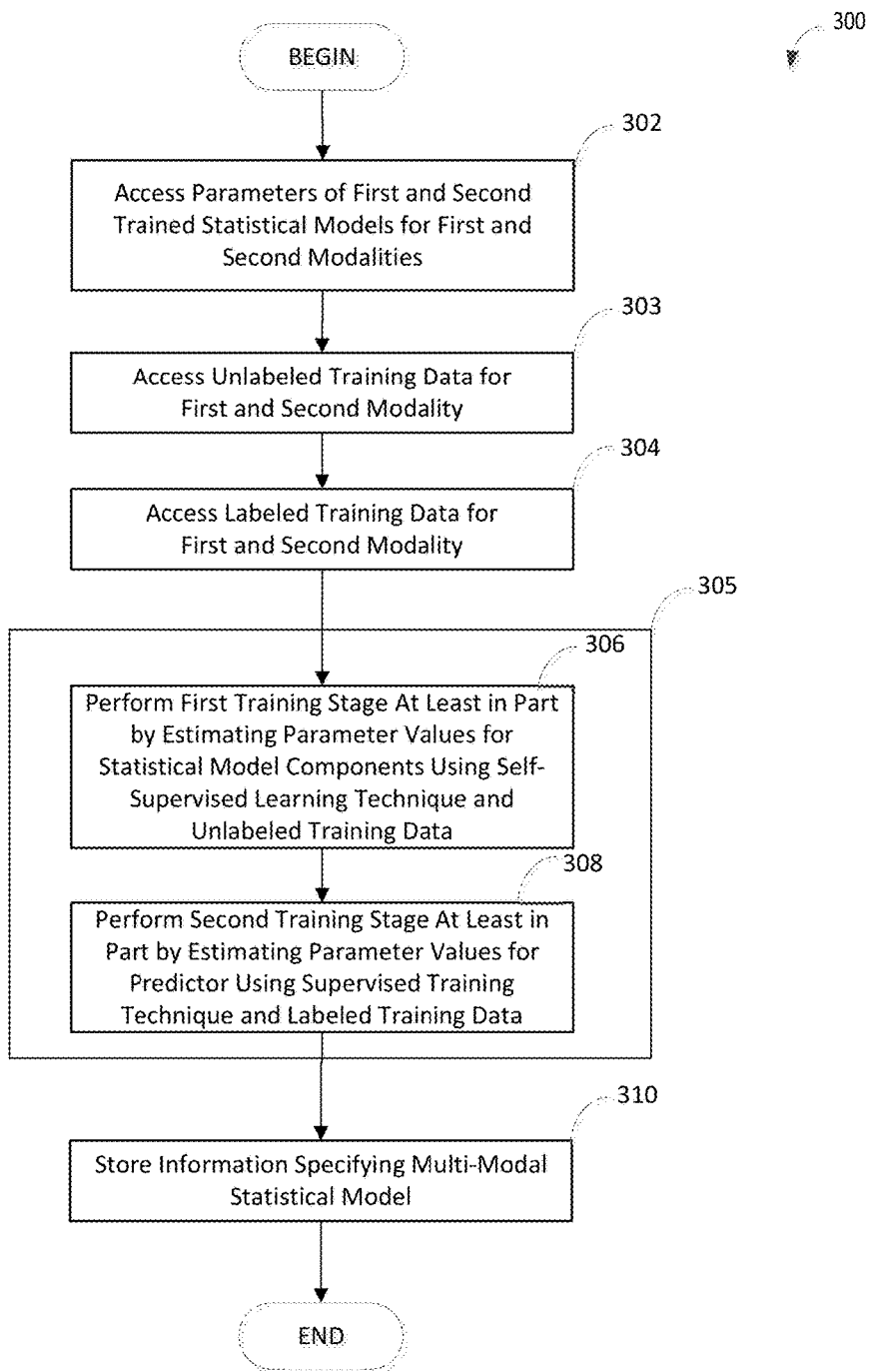
FIG. 3 is a flowchart of an illustrative process for training a multi-modal statistical model using a two-stage training procedure, with the first stage involving self-supervised learning and the second stage involving supervised learning, in accordance with some embodiments of the technology described herein.

FIG. 3 is a flowchart of an illustrative process 300 for training a multi-modal statistical model using a two-stage training procedure, with the first stage involving self-supervised learning and the second stage involving supervised learning, in accordance with some embodiments of the technology described herein. The process 300 may be performed by any suitable computing device(s). For example, the process 300 may be performed by one or more graphics processing units (GPUs), one or more computing device(s) provided by a cloud computing service, and/or any other suitable computing device(s), as aspects of the technology described herein are not limited in this respect.

In the embodiment illustrated in FIG. 3 and described below, process 300 is used to train a multi-modal statistical model configured to receive input from two modalities—a first modality and a second modality. However, it should be appreciated that the process 300 may be used to train a multi-modal statistical model configured to receive input from any suitable number of modalities (e.g., three, four, five, six, seven, eight, nine, ten, eleven, twelve, etc.), as aspects of the technology described herein are not limited in this respect.

In this example, it is assumed that prior to the start of the process 300, individual statistical models have been trained for the first and second modalities. In particular, it is assumed that a first statistical model, including a first encoder and a first decoder, has been trained for the first modality and that a second statistical model, including a second encoder and a second decoder, has been trained for the second modality. The first statistical model may be an auto-encoder type statistical model having been trained using data in the first modality. The second statistical model may be an auto-encoder type statistical having been trained using data in the second modality. However, as described in more detail below, in some embodiments, the individual statistical models may be trained for the first time or at least updated during training of the multi-modal statistical model.

In some embodiments, the multi-modal statistical model being trained during execution of process 300 may comprise an encoder component for each of the modalities, a joint modality representation component, a modality embedding component for each of the modalities, a predictor component, and a task embedding component for each of the modalities, and process 300 may be used to estimate parameter values for each of one or more of these components. For example, the multi-modal statistical model 250 of FIG. 2B comprises encoder 204, encoder 214, knowledge base 230, modality embeddings 232, predictor 252, and task embeddings 254 and parameters of the components 230, 232, 252, and 254 may be estimated as part of process 300. It should be appreciated that the decoders for each of multiple modalities (which may be part of the individual statistical models being integrated) may not be part of the multi-modal statistical model. Notwithstanding, such decoders may be used to train the multi-modal statistical model, in a self-supervised learning stage, as described in more detail below.

Process 300 begins at act 302, where the parameters of a first trained statistical model for a first modality and parameters of a second trained statistical model for a second modality are accessed. The parameters may be accessed from local storage, over a network from remote storage, or any other suitable source.

In some embodiments, the first trained statistical model may include an auto-encoder and may comprise a first encoder and a first decoder, each having a respective set of parameters, which may be accessed at act 302. The first encoder may be configured to receive, as input, data having the first modality and output a latent representation (which may have a lower dimensionality than the dimensionality of the input data) and the first decoder may be configured to reconstruct the input data from the latent representation. In some embodiments, the first trained statistical model may be a neural network (e.g., a feedforward neural network, a convolutional neural network, a recurrent neural network, a fully connected neural network, etc.) and the first encoder and the first decoder may include one or more neural network layers such that the parameters of the first encoder and decoder include weights for each of the neural network layers. Though it should be appreciated that the first trained statistical model is not limited to being a neural network and may be any other suitable statistical model.

In some embodiments, the second trained statistical model may include an auto-encoder and may comprise a second encoder and a second decoder, each having a respective set of parameters, which may be accessed at act 302. The second encoder may be configured to receive, as input, data having the second modality and output a latent representation (which may have a lower dimensionality than the dimensionality of the input data) and the second decoder may be configured to reconstruct the input data from the latent representation. In some embodiments, the second trained statistical model may be a neural network (e.g., a feedforward neural network, a convolutional neural network, a recurrent neural network, a fully connected neural network, etc.) and the second encoder and the second decoder may include one or more neural network layers such that the parameters of the first encoder and decoder include weights for each of the neural network layers. Though it should be appreciated that the second trained statistical model is not limited to being a neural network and may be any other suitable statistical model.

In some embodiments, the first encoder and the second encoder are different from one another since they are configured to receive data of different modalities. In such embodiments, the first and second decoders are different from each other. In some such embodiments, when the encoders are each implemented as neural networks, the neural network architecture for the encoders is different (e.g., different numbers of layers, different types of layers, different dimensionality of layers, different non-linearities, etc.). As one example, the first encoder may be configured to receive, as input, an image and produce a latent representation of the image and the second encoder may be configured to receive, as input text and produce a latent representation of the text. As another example, the first encoder may be configured to receive and produce a latent representation of protein sequence data, and the second encoder may be configured to receive, and produce a latent representation of protein family data. As yet another example, the first encoder may configured to receive and produce a latent representation of a medical image of a first type (e.g., ultrasound) and the second encoder may be configured to receive and produce a latent representation of a medical images of a second type different from the first type (e.g., MRI image).

In some embodiments, the latent representation produced at the output of the first encoder may have the same dimensionality as the latent representation produced at the output of the second encoder. For example, as described in more detail below, the first encoder may receive as input a representation of a protein sequence (e.g., a 20×1024 one-hot-encoded protein sequence) and return a 10×1 latent representation. In this same example, the second encoder may receive as input biological process input (which, for example, may be one-hot-encoded as a 24,937-dimensional vector) and return a 10×1 latent representation. However, it is not a requirement that the latent representations be of the same dimension, as using different modality embeddings provides for the additional flexibility, whereby latent representations for different modalities have different dimensions.

FIG. 2A illustrates one example of the parameters that may be accessed at act 302. In particular, parameters of encoder 204 (first encoder), decoder 210 (first decoder), encoder 214 (second encoder), and decoder 218 may be accessed at act 302.

Next, process 300 proceeds to act 303, where unlabeled training data is accessed for each the first and second modalities. The unlabeled training data accessed at act 303 may be used for the first stage of training the multi-modal statistical model using self-supervised learning at act 306. As part of the first training stage, the unlabeled training data may be used to estimate parameters of one or more components of the multi-modal statistical model, which components allow for integrating the first and second statistical models (whose parameters were accessed at act 302). For example, the multi-modal statistical model (e.g., model 250 shown in FIG. 2B) may include a joint modality representation (e.g., knowledge base 230), a first modality embedding, (e.g., part of modality embeddings 232) and a second modality embedding (e.g., part of modality embeddings 232), and the unlabeled training data may be used to estimate parameters of the joint modality representation, the first modality embedding, and the second modality embedding during act 306.

It should be appreciated that, while the unlabeled training data accessed at act 303 includes training data for each of the first and second modalities, these data need not have been gathered synchronously or in a coordinated fashion. The unlabeled training data for the first modality may have been generated independently from the unlabeled training data for the second modality. The unlabeled training data for different modalities may be generated at different times by different entities and/or may be stored in different databases. There may be more training data for the first modality than for the second or vice versa. Training data for the first and second modality need not be paired—there need not be a one-to-one correspondence. In some embodiments, the training data obtained at act 303 may be labeled, but the labels may be discarded or ignored when the training data is used during the first training stage at act 306.

Next, process 300 proceeds to act 304, where labeled training data is accessed for the first and second modalities. The labeled training data accessed at act 304 may be used for the second stage of training the multi-modal statistical model using supervised learning at act 308.

As part of the second training stage, the labeled training data may be used to estimate parameters of one or more components of the multi-modal statistical model, which components allow for integrating the first and second statistical models (whose parameters were accessed at act 302) and using these models to perform a prediction task. For example, the multi-modal statistical model (e.g. model 250 shown in FIG. 2B) may include a predictor (e.g., predictor 252), a first task embedding, (e.g., part of task embeddings 254) and a second modality embedding (e.g., part of task embeddings 254), and the labeled training data may be used to estimate parameters of the predictor, the first task embedding, and/or the second modality embedding during act 308.

While the labeled training data accessed at act 304 includes training data for each of the first and second modalities, these data need not have been gathered synchronously or in a coordinated fashion. The labeled training data for the first modality may have been generated independently from the labeled training data for the second modality. The labeled training data for different modalities may be generated at different times by different entities and/or may be stored in different databases. There may be more training data for the first modality than for the second or vice versa. Training data for the first and second modality need not be paired—there need not be a one-to-one correspondence.

Next, process 300 proceeds to act 305 where the multi-modal statistical model is trained using a two-stage procedure. Initially, at act 306, the unlabeled data obtained at act 303 is used to estimate parameter values for one or more components of the multi-modal statistical model using a self-supervised learning technique. Next, at act 308, the labeled data obtained at act 304 is used to estimate parameter values for one or more additional components of the multi-modal statistical model using a supervised learning technique. Each of these acts is described in further detail below.

In some embodiments, act 306 may comprise estimating parameter values for one or more components of the multi-modal statistical model using a self-supervised learning technique. In some embodiments, the parameters of the joint modality representation (e.g., knowledge base 230 in the example of FIG. 2B) may be estimated at act 306. Additionally, in some embodiments, parameters of one or more modality embeddings (e.g., one or more of modality embeddings 232) may be estimated at act 306.

In some embodiments, the parameter values estimated as part of act 306 may be estimated using self-supervised learning. Training a statistical model using self-supervised learning may involve training the statistical model to reproduce inputs at the outputs. Accordingly, in some embodiments, a particular piece of data may be provided as input to the statistical model and the output of the statistical model may be compared to the very same particular piece of data. In turn, one or more values of the parameters of the statistical model may be updated (e.g., using stochastic gradient descent or any other suitable training algorithm) based on the difference between the output of the statistical model and the particular piece of data provided to the statistical model, which difference provides a measure of how well the output of the statistical model, when operated with its current set of parameter values, reproduces the input.

In some embodiments, the unlabeled training data accessed at act 303 may be used to estimate parameter values of the joint modality representation and the modality embeddings in the multi-modal statistical model. The parameter values may be estimated using an iterative learning algorithm such as, for example, stochastic gradient descent. The iterative learning algorithm may involve providing at least some of the unlabeled training data as input to the encoders of the multi-modal statistical model, generating output using the respective decoders, comparing the input with the generated output, and updating the parameters values of the joint modality representation and/or the modality embeddings based on the difference between the input and output.

For example, in some embodiments, training data of a first modality may be provided as input to a first encoder for the first modality (e.g., encoder 204). The output of the first encoder (e.g., feature representation 206), the joint modality representation (e.g., knowledge base 230), and the first modality embedding (e.g., one of modality embeddings 232), may be used to generate input (e.g., feature representation 208) to a first decoder for the first modality (e.g., decoder 210). In turn, the output of the decoder 210 may be compared with the input provided to the first encoder and at least some of the parameter values of the joint modality representation and/or the first modality embedding may be updated based on the difference between the input to the first encoder and the output of the first decoder.

In this example, generating the input to the first decoder from the output of the first encoder may include: (1) projecting the joint modality representation to the space of the first modality to obtain a plurality of projected vectors; (2) calculating a distance (e.g., a cosine distance and/or any other suitable type of distance measure) between each of the plurality of projected vectors and the output of the first encoder and using these distances to calculate weights for the projected vectors (e.g., by using a soft-max weighting); and (3) generating input to the first decoder by aggregating, with the output of the first encoder, a weighted sum of the projected vectors weighted by the calculated weights. For example, the joint modality representation may include N m-dimensional vectors (which may be represented and/or stored as an N×m matrix), and projecting the joint modality representation using a first modality projection, which may be represented as an m×d to the first modality may produce N d-dimensional vectors (which may be represented an as an N×d matrix). The distance between the output of the first encoder (e.g., feature representation 206 shown in FIG. 2A) and each of the N d-dimensional vectors may be calculated and used to obtain weights for each of the N d-dimensional vectors. Then the input to the first decoder (e.g., feature representation 208) may be calculated as an aggregation 207 (e.g., sum, product, arithmetic average, geometric average) of the feature representation 206 with the weighted sum of the N d-dimensional vectors, with the vectors being weighted by the calculated weights. In other embodiments, the input the first decoder may be the sum of the output of the first encoder and the N d-dimensional vector closest to the output of the first encoder according to a suitably-chosen distance measure (e.g., cosine distance) rather than a weighted average of multiple d-dimensional vectors in the projected joint modality representation, as aspects of the technology described herein are not limited in this respect. In yet other embodiments, the input to the first decoder may be the weighted sum of the N d-dimensional vectors (calculated as discussed above) or the vector most similar to the output of the first encoder (identified as described above), but without being aggregated with the output of the first encoder.

As another example, in some embodiments, training data of a second modality may be provided as input to a second encoder for the second modality (e.g., encoder 214). The output of the second encoder (e.g., feature representation 216), the joint modality representation (e.g., knowledge base 230), and the second modality embedding (e.g., one of modality embeddings 232), may be used to generate input (e.g., feature representation 218) to a second decoder for the second modality (e.g., decoder 220) using aggregation operation 217. In turn, the output of the decoder 220 may be compared with the input provided to the second encoder and at least some of the parameter values of the joint modality representation and/or the second modality embedding may be updated based on the difference between the input to the second encoder and the output of the second decoder.

In some embodiments, act 308 may comprise estimating parameter values for one or more components of the multi-modal statistical model using a supervised learning technique. In some embodiments, the parameters of a predictor (e.g., predictor 252 in the example of FIG. 2B) may be estimated at act 308. Additionally, in some embodiments, parameters of one or more task embeddings (e.g., one or more of task embeddings 254) may be estimated at act 308.

In some embodiments, the parameter values estimated as part of act 306 may be estimated using supervised learning based on the labeled training data accessed at act 304. In some embodiments, a particular piece of data may be provided as input to the statistical model and the output of the statistical model may be compared to the label for the particular piece of data. In turn, one or more values of the parameters of the statistical model may be updated (e.g., using stochastic gradient descent or any other suitable training algorithm) based on the difference between the output of the statistical model and the label for the particular piece of data provided to the statistical model, which difference provides a measure of how well the output of the statistical model, when operated with its current set of parameter values, reproduces the provided labels.

In some embodiments, the loss (or cost) function used during the second training stage may be selected depending on the type of task for which the predictor component of the multi-modal statistical model is being trained. For example, if the task involves multi-label exclusive classification, cross-entropy loss may be used. As another example, if the task involves prediction of a continuous distribution, Kullback-Leibler divergence may be used at the loss function.

In some embodiments, during performance of the second stage, the parameter values estimated during the first training stage may be fixed. For example, after parameter values for the joint modality representation and modality embeddings are estimated during the first training stage, these values may remain fixed during the second training stage, while parameter values for the predictor and task embeddings are being estimated during the second training stage.

After act 308 completes, thereby completing act 305, the trained multi-modal statistical model may be stored, at act 310, for subsequent use. Storing the trained multi-modal statistical model comprises storing parameter values for one or more components of the multi-modal statistical model. In some embodiments, storing the trained multi-modal statistical model comprises storing parameter values estimated during act 305 for one or more of the following components: joint modality representation, first modality embedding, second modality embedding, predictor, first task embedding, and the second task embedding. The parameter values may be stored in any suitable format, as aspects of the technology described herein are not limited in this respect. The parameter values may be stored using one or multiple computer-readable storage mediums (e.g., one or more memories).

It should be appreciated that the process 300 is illustrative and that there are variations. For example, although process 300 is described with reference to training a multi-modal statistical model configured to receive input having two modalities, the process 300 may be modified to train a multi-modal statistical model configured to receive input from more than two modalities (e.g., three, four, five, six, seven, eight, nine, ten, etc. modalities. In some such embodiments, the joint modality representation and a modality embedding for each of the multiple modalities would be learned during the self-supervised learning stage (act 306).

The predictor and a task embedding for each of the multiple modalities would be learned during the supervised learning stage (act 308).

As described above, in some embodiments, the encoder and decoder for each of the modalities may be learned prior to the execution of process 300. In some embodiments, however, one or more of the encoder(s) and/or decoder(s) may be learned during process 300 such that their parameter values are estimated for the first time and/or updated during process 300.

Additional aspects of the techniques for training a multi-modal statistical model may be appreciated from the following discussion of the self-supervised and supervised training stages.

Self-Supervised Training Phase

Let $x_i \in X_i$ be an input data point for the modality i, and let $t_i \in T_i$ be the compressed representation of $x_i$ such that:

$$t_i = \psi_i(x_i),$$

where $\psi_i$ is the encoding function representing the encoder for the ith modality. Let the joint modality representation (sometimes referred to as a knowledge base herein) be an n×m matrix M, where n denotes the number of entries in the joint modality representation and m denotes the dimensionality of each entry.) The joint modality representation may be linearly projected to the representation space of the ith modality by using the modality embedding $E_i$ (an m×$d_i$ matrix, which is learned during the self-supervised training phase):

$$\tilde{M}_i = M E_i.$$

Then the cosine similarity between the representation $t_i$ and the rows of the projected joint modality representation $\tilde{M}_i$ gives us similarity scores over each entry of the joint modality representation (e.g., each row of the memory matrix), which may then be converted to probability using a softmax function, approximating p (m|t) according to:

$$s_i = \tilde{M}_i t_i$$

$$p(m_k \mid t_i) = \frac{e^{s_{ik}/\tau}}{\Sigma_k e^{s_{ik}/\tau}}$$

where $\tau$ is the temperature variable, accounting for the sharpness/entropy of the distribution. The weighted average of the projected joint modality representation matrix entries $\tilde{t}_i$ is then provided as input to the ith modality decoder $\Phi_i$:

$$\tilde{t}_i = \sum_k p(m_k \mid t_i) m_k$$

$$\hat{x}_i = \Phi_i(\tilde{t}_i)$$

The gradient of the reconstruction loss with respect to at least some of the network parameters (e.g., some or all of the parameter values of the encoder, decoder, joint modality representation, and the modality embedding) is back propagated and the parameters are updated via stochastic gradient descent algorithm:

$$\theta_{j,t+1} = \theta_{j,t} + \lambda \nabla_{\theta_{j,t}} \ell(\hat{x}_i, x_i) + \mu_t$$

where $\theta_{j,t}$ is the $j^{th}$ parameter at time t; $\lambda$ and $\mu$ are the learning rate and momentum parameters, respectively, and l( ) is the loss function. The loss function may be cross-entropy, Kullback-Liebler divergence, L1 distance, L2 distance (Euclidean distance), and/or any other suitable loss function, as aspects of the technology described herein are not limited in this respect.

Supervised Training Stage

We define task as predicting labels or values denoted by y∈Y. In the presence of data pairs $(X_i, Y_j)$, we use the joint modality representation trained during the self-supervised learning stage and encoder $\Psi_i(x_i)$ for $x_i \in X_i$ to generate the representation $t_i \in T_i$ as shown in the equations above. Then a Hadamard product is performed between the feature representation $t_i$ and the task embeddings $U_j$ according to:

$$\tilde{u}_{ij} = u_j \odot \tilde{t}_i$$

Finally for the forward pass, we provide the projected representation to the task predictor $$\Pi_j \hat{y}_j = \pi_j(\tilde{u}_{ij})$$

An appropriate loss function is chosen for task type. For example, if the task is a multi-label exclusive classification, cross-entropy loss may be used. As another example, if the task is a prediction of a continuous distribution, an information-theoretic measure such as Kullback-Leibler divergence may be used as the loss function. Regardless of the choice of the loss function, the gradients of the loss with respect to the parameters of task predictor $\pi_j$ and task embedding $U_j$ may be calculated and back-propagated, as described in the stochastic gradient descent equation shown above.

Using Multi-Modal Statistical Models for Prediction

Figure 4:
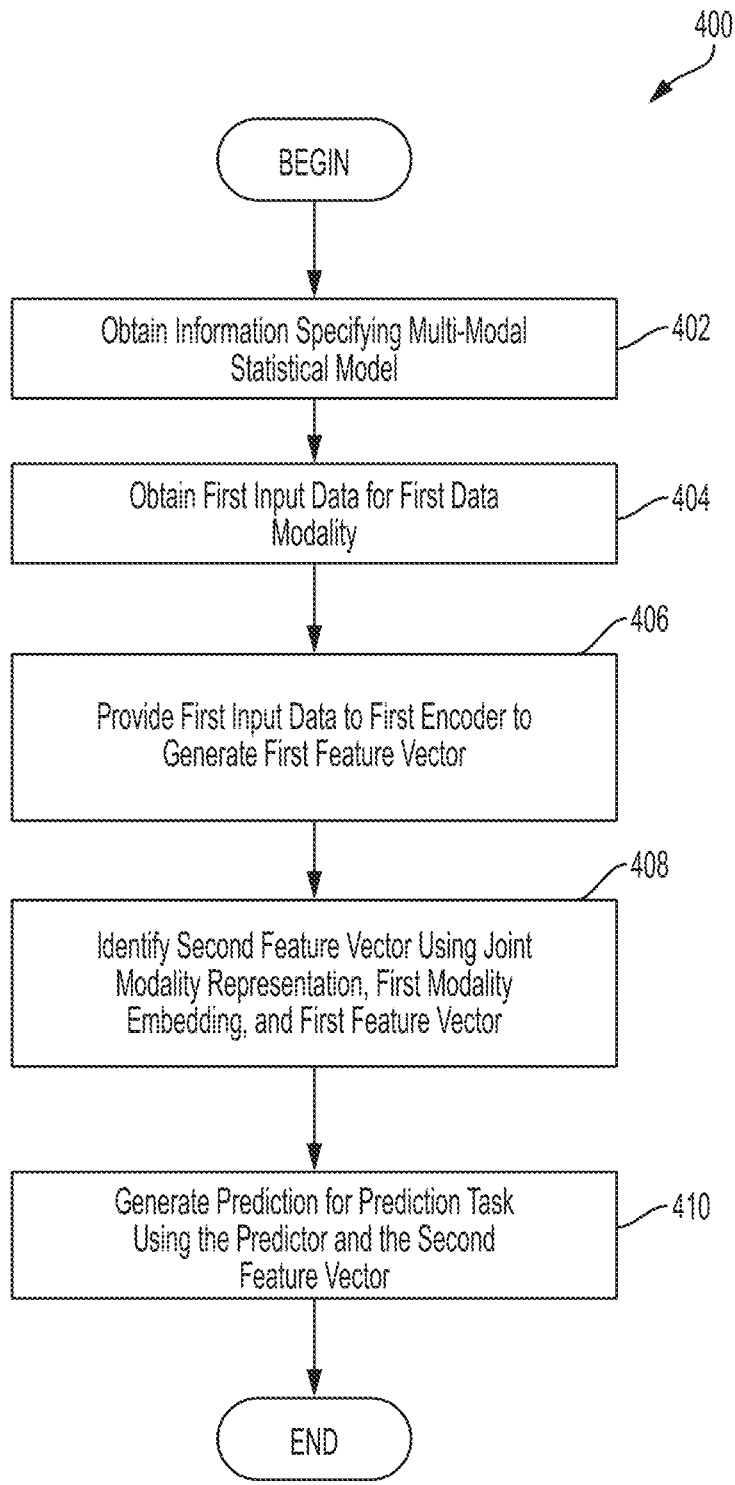
FIG. 4 is a flowchart of an illustrative process 400 for using a multi-modal statistical model for a prediction task, in accordance with some embodiments of the technology described herein.

FIG. 4 is a flowchart of an illustrative process 400 for using a multi-modal statistical model for a prediction task, in accordance with some embodiments of the technology described herein. The process 400 may be performed by any suitable computing device(s). For example, the process 400 may be performed by one or more graphics processing units (GPUs), one or more computing device(s) provided by a cloud computing service, and/or any other suitable computing device(s), as aspects of the technology described herein are not limited in this respect.

In this example, it is assumed that prior to the start of the process 400, a multi-modal statistical model configured to receive input for at least two different modalities has been trained and its parameters have been stored. For example, prior to the start of process 400, a multi-modal statistical model may have been trained using the two-stage training process 300, which is described herein.

Process 400 begins at act 402, where information specifying a previously-trained multi-modal statistical model is accessed. The information specifying the multi-modal statistical model may be in any suitable format and may be accessed from local storage, over a network from remote storage, or any other suitable source(s), as aspects of the technology described herein are not limited in this respect. The information may include values for parameters of the multi-modal statistical model. The multi-modal statistical model may include components having parameters and the information specifying the model may include parameter values for parameters for each of one or more of these components. For example, a multi-modal statistical model may include a joint modality representation, a predictor and, for each of multiple modalities, a respective encoder, a respective modality embedding, and a respective task embedding, and the information accessed at act 402 may include values for these components.

In the embodiment described with reference to FIG. 4, it is assumed that the multi-modal statistical model (for which parameter are accessed) is configured to receive input from two modalities—a first modality and a second modality. However, it should be appreciated that, in other embodiments, the multi-modal statistical model may be configured to receive input from any suitable number of modalities (e.g., three, four, five, six, seven, eight, nine, ten, eleven, twelve, etc.), as aspects of the technology described herein are not limited in this respect.

Next, process 400 proceeds to act 404, where input data is obtained for the first data modality (e.g., protein sequence data). In some embodiments, the input data may be converted or otherwise pre-processed into a representation suitable for providing to the encoder for the first modality. For example, categorical data may be one-hot encoded prior to being provided to the encoder for the first modality. As another example, image data may be resized prior to being provided to the encoder for the first modality. In other embodiments, however, no conversion and/or pre-processing may be required or performed.

Next, process 400 proceeds to act 406, where the input data is provided as input to the first encoder, which generates a first feature vector as output. For example, as shown with reference to FIG. 2B, input 202 for modality "A", is provided as input to the encoder 204 for modality "A", and the encoder 204 produces a first feature vector (e.g., feature representation 206 as output).

Next, process 400 proceeds to act 408, where the first feature vector generated at act 406 (at the output of the first encoder) is used, together with the joint modality representation and the first modality embedding to generate a second feature vector. For example, as shown with reference to FIG. 2B, the first feature vector (e.g., feature representation 206) may be used together with one of the modality embeddings 232 and the knowledge base 230 to identify (e.g., generate or select) the second feature vector (e.g., feature representation 208).

The second feature vector may be identified in any of the ways described herein. For example, in some embodiments, identifying the second feature vector may include: (1) projecting the joint modality representation (e.g., knowledge base 230) to the space of the first modality to obtain a plurality of projected vectors; (2) calculating a distance (e.g., a cosine distance and/or any other suitable type of distance measure) between each of the plurality of projected vectors and the first feature vector (e.g., feature representation 206), and using these distances to calculate weights for the projected vectors (e.g., by using a soft-max weighting); and (3) generating the second feature vector as a weighted sum of the projected vectors weighted by the calculated weights. For example, the joint modality representation may include N m-dimensional vectors (which may be represented and/or stored as an N×m matrix), and projecting the joint modality representation using a first modality projection, which may be represented as an m×d to the first modality may produce N d-dimensional vectors (which may be represented an as an N×d matrix). The distance between the first feature vector output by the first encoder (e.g., feature representation 206 shown in FIG. 2A) and each of the N d-dimensional vectors may be calculated and used to obtain weights for each of the N d-dimensional vectors. Then the second feature vector (e.g., feature representation 208) may be calculated as a weighted sum of the N d-dimensional vectors, with the vectors being weighted by the calculated weights. In other embodiments, the second feature vector may be identified by selecting, from among the N d-dimensional projected vectors, the vector closest to the first feature vector generated by the first encoder according to a suitably-chosen distance measure (e.g., cosine distance), rather than a weighted average of multiple d-dimensional vectors in the projected joint modality representation.

Next, process 400 proceeds to act 410, where the second feature vector is used to generate a prediction for a prediction task using the predictor and a task embedding for the first modality (both of which are components in the multi-modal statistical model). This may be done in any suitable way. For example, the task embedding for the first modality may have a dimensionality that is the same as that of the second feature vector. In this example, the weights of the task embedding may be used to point-wise multiply the values of the second feature vector (e.g., in the sense of a Hadamard product) to generate input to the predictor. In turn, the predictor may output the prediction for the task based on this input. For example, as shown in FIG. 2B, the second feature vector (e.g., representation 208) may be point-wise modified (e.g., multiplied) by the first task embedding of task embeddings 254 and provided as input to predictor 252 to produce an output for prediction task 256.

As may be appreciated from the above description of process 400, the multi-modal statistical model may be used to generate a prediction for a task using input only from a single modality. This means that when inputs are available from multiple different modalities at different times, they may be provided as inputs to the multi-modal statistical model when they become available—asynchronously.

In some embodiments, the multi-modal statistical model may be operated synchronously and may be used to process paired inputs from two modalities or linked inputs from more than two modalities. For example, a first input for the first modality (e.g., input 202) may be provided as input to the encoder for the first modality (e.g., encoder 204) to generate a first feature vector (e.g., feature representation 206), and the first feature vector may be used, together with the joint modality representation (e.g., knowledge base 230) and first modality representation (e.g., of modality representations 232) to identify (e.g., generate or select) a second feature vector (e.g., feature representation 208). In this example, the first input for the first modality (e.g., input 202) may be paired (e.g., provided at the same time as input to the multi-modal statistical model) with first input for the second modality (e.g., input 212). The first input for the second modality (e.g., input 212) may be provided as input to the encoder for the second modality (e.g., encoder 214) to identify (e.g., generate or select) a third feature vector (e.g., feature representation 216), and the first feature vector may be used, together with the joint modality representation (e.g., knowledge base 230) and second modality representation (e.g., of modality representations 232) to generate a fourth feature vector (e.g., feature representation 218).

In turn, the second and fourth feature vectors may be modified by the task embeddings for the first and second modalities, and the result may be combined (e.g., by a coordinate-wise addition 260) and be provided as inputs to the predictor (e.g., predictor 252) to provide a prediction for task 256.

Example: Protein Structure Prediction

In this section, the techniques for unifying deep learning statistical models for different data modalities described herein are illustrated for an example problem of predicting protein structure. Conventional techniques to building predictive models in molecular biology often fall short, with the resulting models lacking desired performance characteristics (e.g., precision).

Building a common framework to accommodate predictive modeling of various types of biological data available is highly challenging for a variety of reasons, including:

Source Heterogeneity: There are potentially thousands of different molecular entities that may be probed and the data we acquire come in various forms or modalities.

High Dimensionality: Observed data sparsely samples the all possible configurations of the input space. Therefore, most of the time the available data are sparse and insufficient.

Experimental Noise: Biological data acquisition is often noisy and suffers from experimental biases and idiosyncrasies Unmatched Modalities and Incompleteness: Experiments and observations are limited to only a couple of modalities at a time, which results in highly incomplete data.

Conventional approaches to building high-quality predictive models in such a challenging modeling context rely on strong priors, which express deep domain-level expertise and knowledge. However, our ability to specify such priors is limited by the amount of domain-level knowledge available. For example, without an extensive domain knowledge, functionally annotating a protein sequence of a newly discovered species can be done by performing a BLAST query (finding the closest known sequences) and transferring the functional assignments from the top hits. However, this approach is reported to be very poor and misleading especially when identifying which biological process the protein of interest is involved in. Better performing models require years of accumulated domain knowledge about proteins, amino acid motifs, their participations in biological processes, and the like.

The techniques described herein address the above-described challenges by accommodating multiple modalities without requiring training data to contain fully matching data points (with each data point including a contribution from each of multiple different modalities). The joint modality representation described herein provides a data-driven prior for cross-modality feature extraction, which regularizes the individual models and alleviates extra compression. Every bit of extra compression is equivalent to having twice as much labeled data.

The techniques described herein are illustrated below on a protein function prediction task. First, we downloaded the Swiss-Prot database, which contains 554,452 proteins, and selected six different data modalities including: (1) protein sequence; (2) pfam domains; (3) biological process ontology; (4) molecular function ontology; (5) cellular component ontology; and (6) the taxonomic family of the species. The functional annotations (ontologies) are highly incomplete and possibly noisy. Proteins which are defined as a test set for the second Critical Assessment of Functional Annotation (CAFA2) consortium were excluded to facilitate evaluation of the results.

Implementation Details

Although functional ontology prediction is our task, we treated these ontologies as individual modalities. In order to apply the techniques described herein to the functional ontology prediction task, we need to specify aspects of the encoders, decoders, the joint modality representation, the modality embeddings, and the task embeddings.

Encoders

In this illustrative example, the encoder for protein sequence inputs includes four convolutional blocks each of which contains a 1D convolution with 10 filters of size 20, followed by a layer normalization, one-dimensional max-pooling of size 3 with stride 3, and a rectified linear unit (ReLU) activation. After the four convolutional blocks, the encoder includes another convolutional layer with 10 kernels of size 11 and an adaptive 1d max-pooling to size 1. As a result, the protein sequence encoder takes 10×1024 one-hot-encoded protein sequence input (if the sequence is shorter than 1024, the input is padded with all zeros) and returns 10×1 latent representation.

We used embedding dictionaries as encoders of categorical data sources. Indexing an embedding dictionary is equivalent to forwarding a one-hot-encoded input data to a linear layer without a bias term, but computationally much more efficient as the input is highly sparse. The sizes of the embedding dictionaries are one more than the number of categories in each modality as the first entry is always reserved for an unknown category or padding index. The actual sizes we used in the experiment are 24937, 9572, 3185, 1779, and 11679 for biological process, molecular function, cellular component, taxonomic family, and pfam domains, respectively. The dimension of the embeddings is chosen to be 10.

Decoders

The protein sequence decoder comprises six consecutive layers of deconvolution blocks. Each block contains a deconvolution operation where the number of filters are 128, the filter size is 6, stride is 3 and both ends are padded with 1, followed by a layer normalization and leaky ReLU activation of slope 0.1.

The decoders of categorical modalities are chosen to be a fully connected linear layers of size 10×N, which takes the representation returned from the joint modality representation (e.g., knowledge base) and returns sigmoid-activated scores over all classes (N is the number of classes in each modalities).

Joint Modality Representation and Modality Projections

The joint modality representation comprises 512 vectors of dimension 64. In this example, these vectors may be stored in a matrix of size 512×64. The rows are L2 normalized after each update. Since there are six modalities in this example, there are six modality embeddings, each of which is represented using a matrix of size 64×10. Each modality embedding projects the joint modality representation into the representation space of the respective modality.

Loss Functions

For sequence reconstruction, we used cross entropy loss calculated for a probability distribution over 20 possible amino acids for every amino acid residue in the sequence. We excluded the padded regions. For 3 ontology modalities and the pfam domain modality, we used max-margin loss with a negative sampling procedure and margin value 1. For the taxonomic family modalities, we used cross entropy.

Training

We used a variant of SGD optimizer called "Adam" with a learning rate of $10^{-3}$, and a batch size of 25. We tested both two different scenarios: (1) Synchronous training with paired data; and (2) Asynchronous training with unpaired data.

When training with paired data, the joint modality representation weights are updated with respect to the sum of the gradients contributed from all reconstruction losses, across all modalities, similar to all other parameters.

When training asynchronously, the parameters for each of the modalities are trained one by one by querying the joint modality representation. The joint modality representation weights are updated every time a modality is trained with its own reconstruction objective. We went over all modalities 3 times and each time trained until their full convergence. We reduced the learning rate on the joint modality representation parameters every time a modality is trained.

Results

Figure 5:
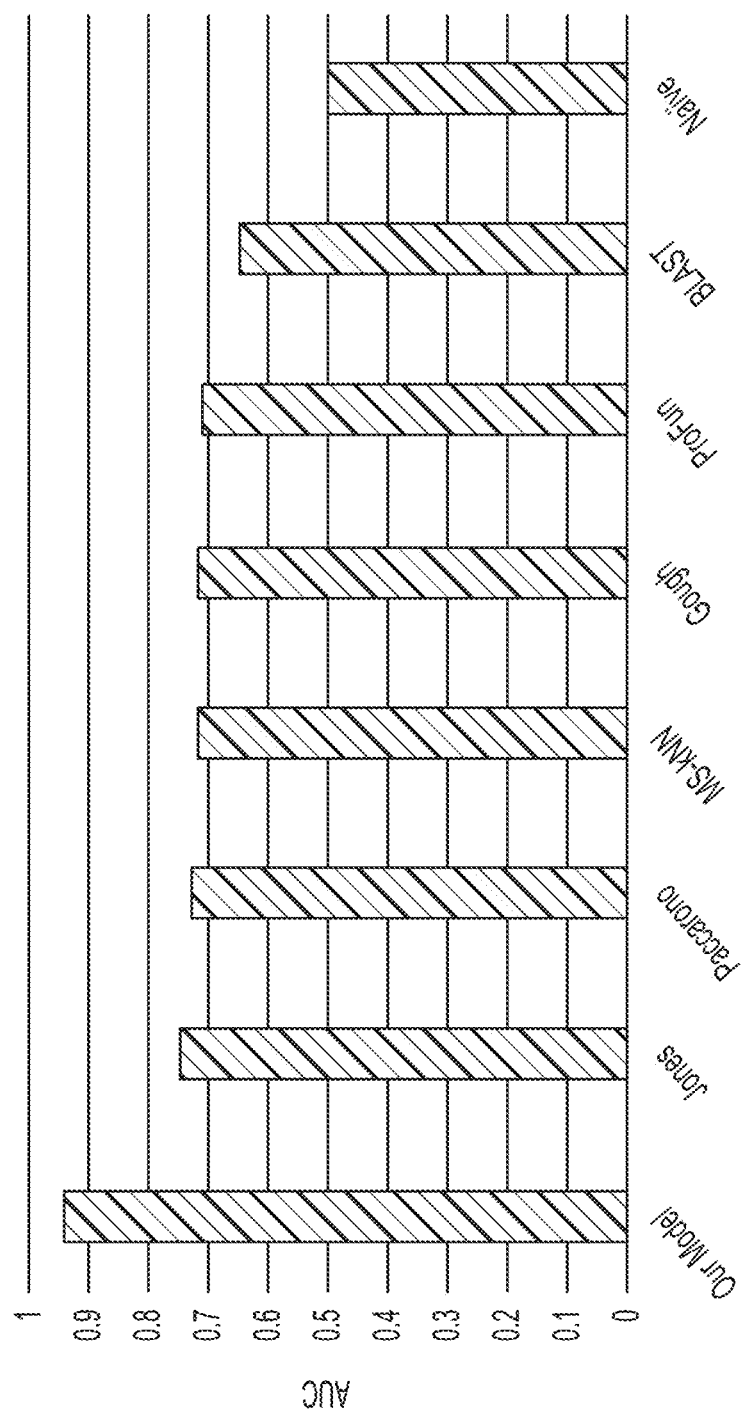
FIG. 5 illustrates the performance of the multi-modal statistical model on a prediction task relative to conventional techniques, in accordance with some embodiments of the technology described herein.

As shown in FIG. 5, the early experiments demonstrate that multi-modal statistical model described above for the functional annotation of proteins performs significantly better than competing conventional approaches other models, all of which requires extensive feature engineering. As shown in FIG. 5, the average AUROC (area under receiver operating characteristic curve) for the multi-modal statistical model described above is higher than that of competing conventional approaches. The performance of the competing approaches shown in FIG. 5 is discussed further in an article titled "An expanded evaluation of protein function prediction methods shows an improvement in accuracy," published on Sep. 7, 2016 in Genome Biology, volume 17, page 184, which article is incorporated by reference herein in its entirety.

Theoretical Underpinnings

Further aspects of the multi-modal statistical models described herein may be appreciated from the following discussion.

Extracting Relevant Information

Let X denote the signal (message) space with a fixed probability measure $\rho(x)$, and the T denote its quantized codebook or compressed representation.

For each $x \in X$ we seek a possibly stochastic mapping to a representative or codeword in a codebook, $t \in T$ characterized by a conditional probability density function (pdf) $p(t|x)$. This mapping induces a soft partitioning of X in which each block is associated with the codebook elements $t \in T$ with probability $p(t|x)$. The total probability of the codeword $t \in T$ is given by:

$$p(t) = \Sigma_x p(t|x)\rho(x).$$

The average volume of the elements of X that are mapped to the same codeword is $2^{H(X|T)}$ where $$H(X|T) = \sum_t p(t)H(X|T=t) = -\sum_t p(t) \sum_x p(x|t)\log(p(x|t))$$

The quality of quantization is determined by the "rate" or "average bits per message" needed to specify an element in the codebook without confusion. This number per element of X is bounded from below by the mutual information $$I(X;T) = \sum_{x \in X} \sum_{t \in T} p(x,t)\log\left(\frac{p(x|t)}{p(t)}\right)$$

This equation may be thought as the average cardinality of the partitioning of X which is given by the ratio of volume of X to that of the mean partition, i.e.

$$K = \frac{2^{H(X)}}{2^{H(X|T)}} = 2^{I(X;T)}$$

Information Bottleneck

Ultimately, for any predictive task, we would like to learn a mapping $p(t|x)$ from an input space X to a representation space T which only retain the relevant information for the prediction (label) space Y. In other words, we would like to minimize the mutual information between X and T while maximizing the mutual information between T and Y which can be captured by minimizing the following functional with respect to the mapping $p(t|x)$:

$$L[p(t|x)] = I(X;T) - \beta I(Y;T)$$

where $\beta$ is the tradeoff parameter.

Input Compression Bound

For the best prediction performance, our objective is to maximize $I(T;Y)$ which is restricted to the upper bound $I(T;Y) \leq I(X;Y)$ due to the data processing inequality. If we had unlimited amount of data in X and Y, we could approximate the joint distribution $p(x,y)$ arbitrarily well and therefore, we would not need a compact representation of X. However, because the amount of data is often limited, $\rho(x|y)$ cannot be estimated sufficiently well. Therefore, we have to regularize the model by compressing the input—reducing the complexity by minimizing $I(X;T)$.

Let $\hat{I}$ denote the empirical estimate of the mutual information from the limited samples. The generalization bound has been shown to be:

$$I(T;Y) \leq \hat{I}(T;Y) + O\left(\frac{|T||Y|}{\sqrt{n}}\right)$$

and $$I(T;X) \leq \hat{I}(T;X) + O\left(\frac{|T|}{\sqrt{n}}\right)$$

Notably, the upper bound depends on the cardinality of the representation $K = |T|2^{I(T;X)}$. In other words, an additional single bit of extra compression is equivalent to doubling the size of data for the same generalization gap.

Compression for Multi-Modal Prediction

Figure 6B:
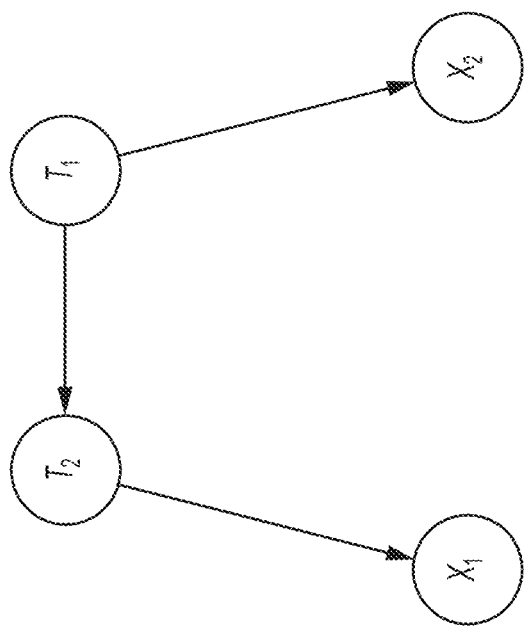
FIGS. 6A and 6B illustrate encoders and decoders, in accordance with some embodiments of the technology described herein.
Figure 6A:
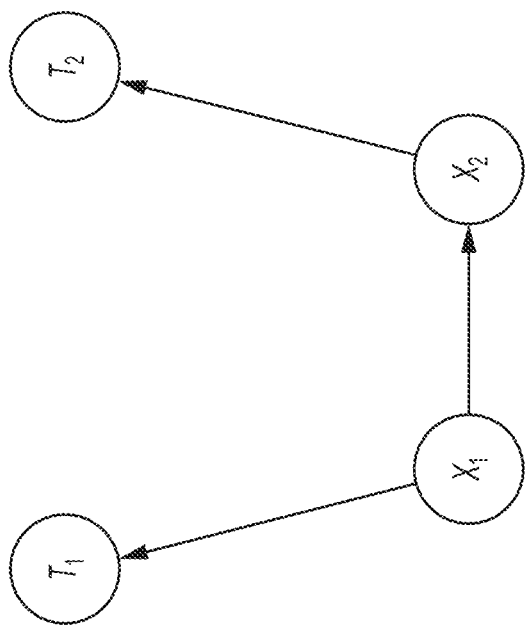

Consider a simple cross-modality prediction setting, where modalities $X_1$ and $X_2$ are compressed into $T_1$ and $T_2$ representations, which are supposed to predict $X_2$ and $X_1$, respectively. As shown in FIG. 6A, the observed variables $X_1$ and $X_2$ are represented by latent random variables $T_1$ and $T_2$, which are compressed representations of $X_1$ and $X_2$. The latent random variables $T_1$ and $T_2$ for first and second modalities may be defined as the outputs of encoders for the first and second modalities, respectively. As shown in FIG. 6B, the latent random variables $T_1$ and $T_2$ may be used to predict the variables $X_1$ and $X_2$. The decoders for the first and second modalities, respectively, may be used to predict the variables $X_1$ and $X_2$ from the latent representations $T_1$ and $T_2$.

In this situation, the Lagrangian to minimize is given by:

$$L = I(T_1;X_1) + I(T_2;X_2) - \gamma I(T_1;T_2)$$

Therefore, while we are compressing, we also want to make sure that the compressed representations $T_1$ and $T_2$ are as informative about one other as possible. This equation indicates that we should maximally compress $X_1$ and $X_2$ by minimizing the mutual information between $X_1$, $T_1$ and $X_2$, $T_2$, while maximizing the mutual information (correlation) between $T_1$ and $T_2$. In the framework described herein, maximizing the mutual information between $T_1$ and $T_2$ may be achieved by forcing each encoded input to be matched to a single or a weighted average of code-words in a codebook—the joint modality representation (e.g., knowledge base 230); the matched entry is then provided as input to the decoder during the self-supervised training stage.

Intuitively, by learning a cross-modality driven compressed representations, we are leveraging the labeled (or paired) data across many modalities, which reduces the generalization gap.

Figure 7:
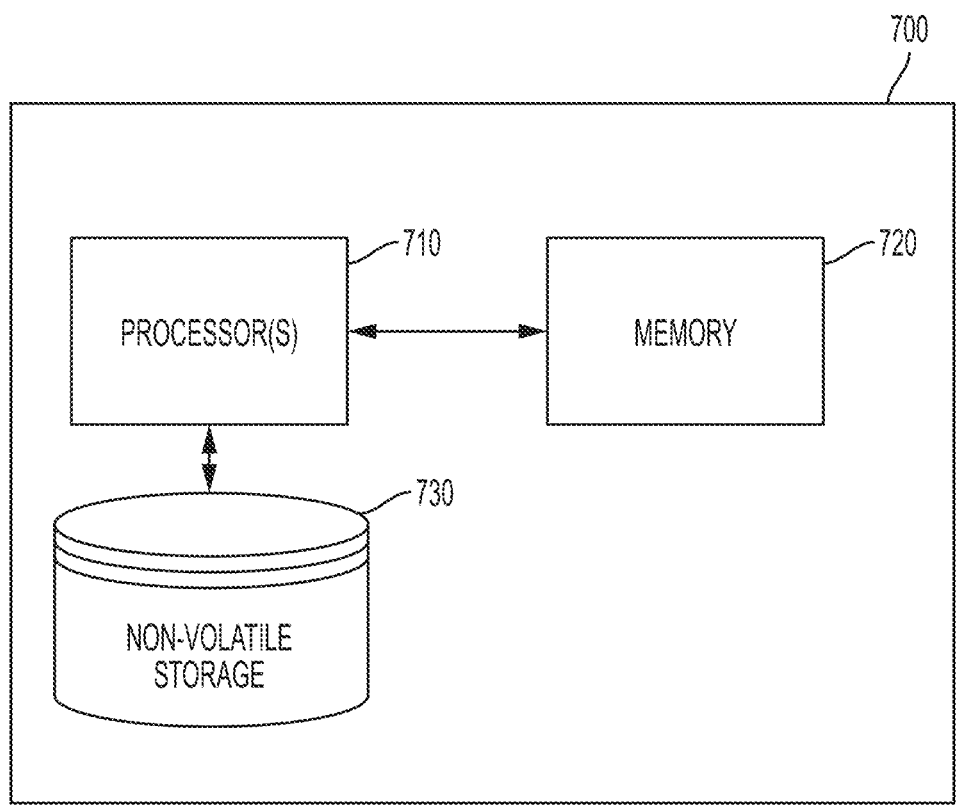
FIG. 7 shows components of an illustrative computer system on which some embodiments of the technology described herein may be implemented.

An illustrative implementation of a computer system 700 that may be used in connection with any of the embodiments of the disclosure provided herein is shown in FIG. 7. The computer system 700 may include one or more computer hardware processors 700 and one or more articles of manufacture that comprise non-transitory computer-readable storage media (e.g., memory 720 and one or more non-volatile storage devices 730). The processor(s) 710 may control writing data to and reading data from the memory 720 and the non-volatile storage device(s) 730 in any suitable manner. To perform any of the functionality described herein, the processor(s) 710 may execute one or more processor-executable instructions stored in one or more non-transitory computer-readable storage media (e.g., the memory 720), which may serve as non-transitory computer-readable storage media storing processor-executable instructions for execution by the processor(s) 710.

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term). The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method for training a multi-modal statistical model configured to receive input data from multiple modalities including input data from a first modality and input data from a second modality different from the first modality, the method comprising:
   accessing training data including training data for the first modality and training data for the second modality;
   training the multi-modal statistical model using the training data, the multi-modal statistical model comprising multiple components including first and second encoders for processing input data for the first and second modalities, respectively, first and second modality embeddings, a joint-modality representation, and a predictor, wherein the first and second modality embeddings comprise a plurality of weights and vectors for projecting the joint-modality representation into respective first and second modality spaces, the training comprising:
    estimating values for parameters of the multiple components using the training data; and
    storing information specifying the multi-modal statistical model at least in part by storing the estimated values for the parameters of the multiple components of the multi-modal statistical model.

2. The method of claim 1, wherein training the multi-modal statistical model further comprises estimating values for parameters of the first and second encoders prior to estimating values for parameters of the first and second modality embeddings, the joint-modality representation, and the predictor.

3. The method of claim 2, wherein training the multi-modal statistical model further comprises estimating values for parameters of first and second decoders for the first and second modalities.

4. The method of claim 1, wherein training the multi-modal statistical model further comprises estimating values for parameters of the first and second encoders jointly with estimating values of parameters of the joint modality representation.

5. The method of claim 4, wherein training the multi-modal statistical model further comprises estimating values for parameters of a first decoder for the first modality and a second decoder for the second modality.

6. The method of claim 1, training the multi-modal statistical model further comprises:
    accessing a first data input in the training data for the first modality;
    providing the first data input to the first encoder to generate a first feature vector;
    identifying a second feature vector using the joint-modality representation, the first modality embedding and the first feature vector;
    providing the second feature vector as input to a first decoder to generate a first data output.

7. The method of claim 6, further comprising:
    comparing the first data output with the first data input; and
    updating at least one value of at least one parameter of the joint-modality representation based on results of the comparison.

8. The method of claim 6, wherein the first encoder is configured to output a d-dimensional vector, and wherein the joint-modality representation comprises Nm-dimensional vectors, and wherein the first modality embedding comprises m*d weights.

9. The method of claim 8, wherein identifying the second feature vector using the joint-modality representation, the first feature vector, and the first modality embedding comprises:
    projecting the joint modality representation to a space of the first modality by using the first modality embedding to obtain N d-dimensional vectors; and
    identifying, from among the N d-dimensional vectors in the joint-modality representation, a third feature vector most similar to the first feature vector according to a similarity metric; and
    generating the second feature vector by aggregating the first feature vector with the third feature vector.

10. The method of claim 8, wherein identifying the second feature vector using the joint-modality representation, the first feature vector, and the first modality embedding comprises:
    projecting the joint modality representation to a space of the first modality by using the first modality embedding to obtain N d-dimensional vectors;
    calculating weights for at least some of the N d-dimensional vectors in the joint modality representation according to a similarity between the at least some of the N d-dimensional vectors and the first feature vector; and
    generating the second feature vector by aggregating the first feature vector with the weighted sum of the at least some of the N d-dimensional vectors weighted by the calculated weights.

11. The method of claim 1, wherein training the multi-modal statistical model comprises:
    performing a first training stage at least in part by estimating values for parameters of the first and second modality embeddings, and the joint modality representation; and
    performing a second training stage at least in part by estimating values parameters of the predictor.

12. The method of claim 1, wherein the multi-modal statistical model further comprises first and second task embeddings, wherein training the multi-modal statistical model further comprises estimating values for parameters of the first and second task embeddings jointly with estimating values for parameters of the predictor.

13. The method of claim 1, wherein the first encoder comprises a neural network.

14. The method of claim 13, wherein the neural network is a convolutional neural network.

15. The method of claim 13, wherein the neural network is a recurrent neural network.

16. The method of claim 1, wherein the training data for the first modality comprises images.

17. The method of claim 16, wherein the training data for the second modality comprises text.

18. A system, comprising:
    at least one computer hardware processor; and
    at least one non-transitory computer-readable storage medium storing processor-executable instructions that, when executed by the at least one computer hardware processor, cause the at least one computer hardware processor to perform a method for training a multi-modal statistical model configured to receive input data from multiple modalities including input data from a first modality and input data from a second modality different from the first modality, the method comprising:
    accessing training data including training data for the first modality and training data for the second modality;
    training the multi-modal statistical model in two stages, the multi-modal statistical model comprising multiple components including first and second encoders for processing input data for the first and second modalities, respectively, first and second modality embeddings, a joint-modality representation, and a predictor, wherein the first and second modality embeddings comprise a plurality of weights and vectors for projecting the joint-modality representation into respective and second modality spaces, the training comprising:
        estimating values for parameters of the multiple components using the training data; and storing information specifying the multi-modal statistical model at least in part by storing the estimated values for the parameters of the multiple components of the multi-modal statistical model.

19. The system of claim 18, wherein training the multi-modal statistical model comprises:
   performing a first training stage at least in part by estimating values for parameters of the first and second modality embeddings, and the joint modality representation; and
   performing a second training stage at least in part by estimating values parameters of the predictor.

20. At least one non-transitory computer-readable storage medium storing processor-executable instructions that, when executed by at least one computer hardware processor, cause the at least one computer hardware processor to perform a method for training a multi-modal statistical model configured to receive input data from multiple modalities including input data from a first modality and input data from a second modality different from the first modality, the method comprising:
   accessing training data including training data for the first modality and training data for the second modality;
   training the multi-modal statistical model in two stages, the multi-modal statistical model comprising multiple components including first and second encoders for processing input data for the first and second modalities, respectively, first and second modality embeddings, a joint-modality representation, and a predictor, wherein the first and second modality embeddings comprise a plurality of weights and vectors for projecting the joint-modality representation into respective first and second modality spaces, the training comprising:
      estimating values for parameters of the multiple components using the training data; and
   storing information specifying the multi-modal statistical model at least in part by storing the estimated values for the parameters of the multiple components of the multi-modal statistical model.

* * * * *